(12) United States Patent
Klug et al.

(10) Patent No.: US 7,166,589 B2
(45) Date of Patent: Jan. 23, 2007

(54) QUINOLINE DERIVATIVES

(75) Inventors: Michael G. Klug, Brooklyn Park, MN (US); Patrizio Mattei, Riehen (CH); Werner Mueller, Aesch (CH); Werner Neidhart, Hagenthal le Bas (FR); Matthias Heinrich Nettekoven, Grenzach-Wyhlen (DE); Philippe Pflieger, Schwoben (FR); Jean-Marc Plancher, Knoeringue (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/376,976

(22) Filed: Mar. 16, 2006

(65) Prior Publication Data

US 2006/0148794 A1 Jul. 6, 2006

Related U.S. Application Data

(60) Division of application No. 11/272,207, filed on Nov. 10, 2005, now Pat. No. 7,064,134, which is a division of application No. 10/896,445, filed on Jul. 22, 2004, now Pat. No. 7,012,073, which is a continuation of application No. 10/247,009, filed on Sep. 19, 2002, now Pat. No. 6,787,558.

(30) Foreign Application Priority Data

Sep. 28, 2001 (EP) .................... 01123496

(51) Int. Cl.
- C07D 403/04 (2006.01)
- C07D 403/14 (2006.01)
- A61K 31/551 (2006.01)
- A61P 3/04 (2006.01)

(52) U.S. Cl. .................... 514/218; 540/553; 540/575

(58) Field of Classification Search ................ 540/553, 540/575; 514/218

See application file for complete search history.

(56) References Cited

U.S. PATENT DOCUMENTS

| 3,272,824 A | 9/1966 | Frederick et al. |
| 4,035,367 A | 7/1977 | Simpson |
| 4,598,089 A | 7/1986 | Hadvary et al. |
| 6,004,996 A | 12/1999 | Shah et al. |

FOREIGN PATENT DOCUMENTS

| EP | 185 359 | 6/1986 |
| EP | 189 577 | 8/1986 |
| EP | 443 449 | 8/1991 |
| EP | 524 495 | 1/1993 |
| EP | 882 717 | 12/1998 |
| WO | WO 99/34786 | 7/1999 |
| WO | WO 00/09122 | 2/2000 |
| WO | WO 0009123 | 2/2000 |
| WO | WO 01 23389 | 4/2001 |
| WO | WO 02 20488 | 3/2002 |

*Primary Examiner*—Kahsay Habte
(74) *Attorney, Agent, or Firm*—George W. Johnston; Patricia S. Rocha-Tramaloni; Brian C. Remy

(57) ABSTRACT

Compounds of formula I

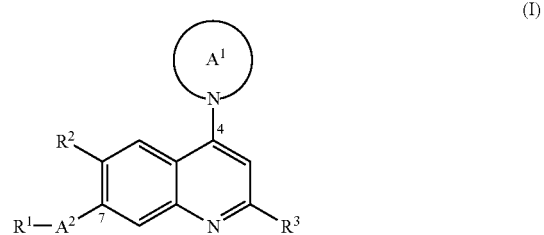

as well as pharmaceutically acceptable salts and esters thereof, wherein $R^1$, $R^2$, $R^3$, $A^1$ and $A^2$ have the significance given in claim 1, can be used in the form of pharmaceutical preparations for the treatment or prevention of arthritis, cardiovascular diseases, diabetes, renal failure, eating disorders and obesity.

19 Claims, No Drawings

QUINOLINE DERIVATIVES

PRIORITY TO RELATED APPLICATIONS

This application is a division of U.S. application Ser. No. 11/272,207, filed Nov. 10, 2005, now allowed; now U.S. Pat. No. 7,064,134 which is a division of U.S. application Ser. No. 10/896,445, filed Jul. 22, 2004, now U.S. Pat. No. 7,012,073, which is a continuation of U.S. application Ser. No. 10/247,009, filed Sep. 19, 2002, now U.S. Pat. No. 6,787,558, which claims the benefit of European Application No. 01123496.0, filed Sep. 28, 2001. The entire contents of the above-identified applications are hereby incorporated by reference.

BACKGROUND OF THE INVENTION

The present invention is concerned with novel quinoline derivatives useful as neuropeptide Y (NPY) receptor ligands, particularly neuropeptide Y (NPY) antagonists, and even more particularly selective neuropeptides Y Y5 receptor antagonists. Accordingly, the compounds of the present invention, their salts and esters can be used in the prophylaxis or treatment of arthritis, cardiovascular diseases, diabetes, renal failure and particularly eating disorders and obesity.

Neuropetide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonise neuropetide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on con associated risk factors such as arthritis, cardiovascular diseases, diabetes and renal failure.

SUMMARY OF THE INVENTION

Briefly stated, the present invention relates to the compounds of formula I and their aforementioned salts and esters per se and their use as therapeutically active substances, a process for the manufacture of the said compounds, intermediates, pharmaceutical compositions, medicaments comprising the said compounds, their pharmaceutically acceptable salts and esters, the use of the said compounds, salts and esters for the prophylaxis and/or therapy of illnesses, especially in the treatment or prophylaxis of arthritis, cardiovascular diseases, diabetes, renal failure and particularly eating disorders such as hyperphagia and particularly obesity, and the use of the said compounds, salts and esters for the production of medicaments for the treatment or prophylaxis of arthritis, cardiovascular diseases, diabetes, renal failure and particularly eating disorders and obesity.

According to one aspect of the present invention, there is provided a compound of formula I

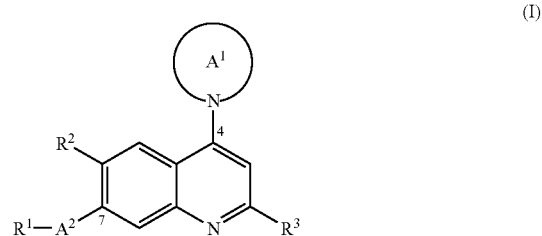

wherein $R^1$, $R^2$, $R^3$, $A^1$ and $A^2$ are as described herewithin.

According to other aspects of the present invention, there is provided a process for making the compounds of formula (I); a method of treating or preventing an illness caused by disorders associated with the NPY receptor comprising administering to a patient in need of such treatment, an effective amount of a compound of the following formula I; and a pharmaceutical composition containing a compound of formula (I) with a pharmaceutically acceptable carrier.

DETAILED DESCRIPTION OF THE INVENTION

The present invention provides a compound of formula I

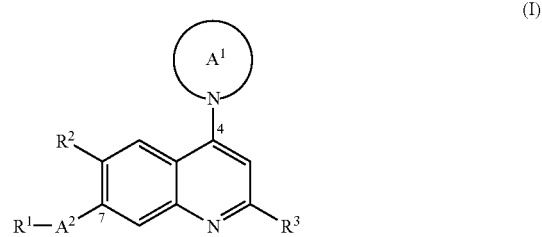

wherein
$R^1$ is —O—$R^4$ or —$NR^5R^6$;
$R^2$ is hydrogen, alkyl, cycloalkyl, alkoxy, halogen, heterocyclyl or amino;
$R^3$ is hydrogen, alkyl, amino or halogen;
$R^4$ is hydrogen, alkyl, cycloalkyl, aryl, aralkyl, cycloalkylalkyl, alkoxyalkyl, hydroxyalkyl or heterocyclyl;
$R^5$ and $R^6$ are independently selected from the group consisting of hydrogen, alkyl, cycloalkyl, aryl, aralkyl, cycloalkylalkyl, alkoxyalkyl, hydroxyalkyl and heterocyclyl;
or $R^5$ and $R^6$ together with the N atom to which they are attached form a 5- to 10-membered heterocyclic ring optionally comprising a second heteroatom selected from nitrogen, oxygen or sulfur and, wherein the heterocyclic ring is optionally substituted with one or more substituents independently selected from alkyl or alkoxy;
$A^1$ is a 5- to 7-membered saturated heterocyclic ring comprising the nitrogen atom which is attached to the quinoline ring and optionally a second heteroatom which is selected from oxygen, sulfur or nitrogen and, wherein the ring is optionally substituted by one to three substituents independently selected from the group consisting of alkyl, alkoxy, hydroxy, hydroxyalkyl, alkoxyalkyl, amino, acetylamino, cyano, tetrahydropyranyloxyalkyl and cycloalkylalkoxy;

$A^2$ is —$CH_2$— or —C(O)—;

and pharmaceutically acceptable salts and esters thereof.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, 2-hydroxyethoxy, 2-methoxyethoxy, preferably methoxy and ethoxy and most preferred methoxy.

The term "aryl", alone or in combination, signifies a phenyl or naphthyl group, preferably a phenyl group which optionally carries one or more, preferably one to three substituents each independently selected from halogen, trifluoromethyl, amino, alkyl, alkoxy, aryloxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, heterocyclylcarbonyl and the like. A preferred heterocyclylcabonyl group is pyrrolidinecarbonyl. Preferred substituents of aryl, preferably phenyl are independently selected from halogen, trifluoromethyl, alkyl, alkoxy, cyano, nitro and pyrrolidine-C(O)—. Examples of aryl are 2-cyanophenyl, 3-cyanophenyl, 4-cyanophenyl, trifluorophenyl, methoxyphenyl, chloro-cyanophenyl, trifluoro-cyanophenyl and dicyanophenyl.

The term "aralkyl", alone or in combination, signifies an alkyl or cycloalkyl group as previously defined, preferably an alkyl group in which one hydrogen atom has been replaced by an aryl group as previously defined. Preferred are benzyl, benzyl substituted with hydroxy, alkoxy or halogen, preferably fluorine.

The term "heterocyclyl", alone or in combination, signifies a saturated, partially unsaturated or aromatic 4- to 10-membered heterocycle which contains one or more, preferably one ore two hetero atoms selected from nitrogen, oxygen and sulfur, wherein oxygen and particularly nitrogen are preferred. If desired, it can be substituted on one or more carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, morpholinyl, piperazinyl, 3,4-dihydro-1H-iso-quinolinyl, azepanyl or tetrahydropyranyl, wherein each of these rings can be substituted with alkyl. Particularly preferred are pyrrolidinyl, pyridinyl and tetrahydropyranyl, particularly tetrahydropyran-2-yl. The term 5- to 10-membered heterocyclic ring as used in the definition of $R^5$ and $R^6$ signifies a saturated, partially unsaturated or aromatic 5- to 10-membered mono or bicyclic heterocycle such as for example pyrrolidine, piperidine and piperazine.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably amino, dimethylamino and diethylamino and particularly preferred primary amino.

The term "halogen" signifies fluorine, chlorine, bromine or iodine and preferably fluorine, chlorine or bromine and particularly chlorine.

The term "cyano", alone or in combination, signifies a —CN group.

The term "nitro", alone or in combination, signifies a —$NO_2$ group.

Examples of pharmaceutically acceptable salts of the compounds of formula I are salts with physiologically compatible mineral acids such hydrochloric acid, sulfuric acid or phosphoric acid; or with organic acids such as methanesulfonic acid, formic acid, acetic acid, trifluoroacetic acid, citric acid, fumaric acid, maleic acid, tartaric acid, succinic acid or salicylic acid. Preferred is oxalic acid. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions. Preferred salts are salts with oxalic acid, hydrochloride salts and formate salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes pharmaceutically acceptable solvates.

The term pharmaceutically acceptable esters of the compounds of formula I means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

In the nomenclature used in the present application the ring atoms of the quinoline ring are numbered as follows:

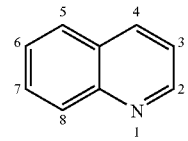

wherein, $R^3$ is attached at the 2-position and $R^2$ is attached at the 6-position.

Preferred are compounds of formula I and pharmaceutically acceptable salts thereof. Particularly preferred are the compounds of formula I.

Preferred are compounds of formula I, wherein $R^1$ is —O—$R^4$ or —$NR^5R^6$;

$R^2$ is hydrogen, alkyl, cycloalkyl, alkoxy, halogen, heterocyclyl or amino;

$R^3$ is hydrogen, alkyl, amino or halogen;

$R^4$ is hydrogen, alkyl, cycloalkyl, aryl, aralkyl, cycloalkylalkyl, alkoxyalkyl, hydroxyalkyl or heterocyclyl;

$R^5$ and $R^6$ are independently selected from hydrogen, alkyl, cycloalkyl, aryl, aralkyl, cycloalkylalkyl, alkoxyalkyl, hydroxyalkyl and heterocyclyl;

or $R^5$ and $R^6$ together with the N atom to which they are attached form a 5- to 10-membered heterocyclic ring optionally comprising a second heteroatom selected from nitrogen, oxygen or sulfur and, wherein the heterocyclic ring is optionally substituted with one or more substituents independently selected from alkyl and alkoxy;

$A^1$ is a 5- to 7-membered saturated heterocyclic ring comprising the nitrogen atom which is attached to the quinoline ring and optionally a second heteroatom which is selected from oxygen, sulfur or nitrogen and, wherein the ring is optionally substituted by one to three substituents independently selected from alkyl, alkoxy, hydroxy, hydroxyalkyl, alkoxyalkyl, amino, acetylamino and cyano;

$A^2$ is —$CH_2$— or —(O)—;

and pharmaceutically acceptable salts and esters thereof.

Preferred are compounds according to formula I, wherein $R^2$ is hydrogen, alkyl, alkoxy or halogen. Particularly preferred are compounds of formula I, wherein $R^2$ is hydrogen or methyl. Very preferred are compounds according to formula I, wherein $R^2$ is hydrogen.

Also preferred are compounds of formula I, wherein $R^1$ is —O—$R^4$.

Another preferred aspect of the present invention are compounds according to formula I, wherein $R^1$ is —$NR^5R^6$.

Further preferred are the compounds of formula I, wherein $R^3$ is hydrogen, methyl, methylamino, dimethylamino or chloro.

Likewise preferred are compounds according to formula I, wherein $R^3$ is hydrogen or alkyl. Particularly preferred is alkyl. Very preferred is methyl and ethyl. Most preferred is methyl.

Also preferred are compounds according to formula I, wherein $R^4$ is hydrogen, alkyl, aryl, alkoxyalkyl or heterocyclyl. Particularly preferred are compounds according to formula I, wherein $R^4$ is hydrogen, alkyl, alkoxyalkyl, pyridinyl, pyrrolidinyl, tetrahydropyranyl, phenyl, phenyl substituted with one to three substituents independently selected from alkyl, cyano, trifluoromethyl, alkoxy, halogen, pyrrolidinylcarbonyl and nitro.

Particularly preferred are compounds according to formula I, wherein $R^4$ is hydrogen, alkyl, alkoxyalkyl, pyridinyl, pyrrolidinyl, phenyl, phenyl substituted with one to three substituents independently selected from alkyl, cyano, trifluoromethyl, alkoxy, halogen, pyrrolidinylcarbonyl and nitro.

Preferred are compounds according to formula I, wherein $R^5$ and $R^6$ are independently selected from hydrogen, alkyl, aryl or alkoxyalkyl, or $R^5$ and $R^6$ together with the N atom to which they are attached form a 5- or 6-membered heterocyclic ring optionally comprising a second heteroatom selected from nitrogen or oxygen and wherein the heterocyclyc ring is optionally substituted with one or more, preferably one to three substituents independently selected from alkyl and alkoxy. Examples of such 5- to 6-membered heterocyclic rings are pyrrolidine, piperidine and piperazine, preferably pyrrolidine and piperidine. Further preferred are compounds according to formula I, wherein $R^5$ and $R^6$ are independently selected from hydrogen, alkyl, aryl or alkoxyalkyl, or $R^5$ and $R^6$ together with the N atom to which they are attached form a 5- or 6-membered heterocyclic ring and, wherein the heterocyclyc ring is optionally substituted with one or more, preferably one to three substituents independently selected from alkyl and alkoxy. Particularly preferred are compounds according to formula I, wherein one of $R^5$ and $R^6$ is hydrogen, aryl or alkoxyalkyl and the other is hydrogen or alkyl; or $R^5$ and $R^6$ together with the N atom to which they are attached form a pyrrolidine ring.

Further preferred are the compounds of formula I, wherein $A^1$ is a 5- to 7-membered saturated heterocyclic ring comprising the nitrogen atom which is attached to the quinoline ring and optionally a second heteroatom which is selected from oxygen, sulfur and nitrogen and, wherein the ring is optionally substituted by alkyl, hydroxy, hydroxymethyl, amino, alkoxy, tetrahydropyranyloxyalkyl or cycloalkylalkoxy, preferrably by alkyl, amino, tetrahydropyranyloxymethyl or cyclopropylmethoxy.

Also preferred are the compounds of formula I, wherein $A^1$ is a 5- to 7-membered saturated heterocyclic ring comprising the nitrogen atom which is attached to the quinoline ring and optionally a second heteroatom which is selected from oxygen, sulfur and nitrogen and, wherein the ring is optionally substituted by alkyl, hydroxy, hydroxymethyl, amino, or alkoxy, preferrably by alkyl or amino. Examples of such 5- to 7-membered saturated heterocyclic rings are pyrrolidine, piperidine, azepane, piperazine and a [1,4]diazepane ring. Particularly preferred are compounds of formula I, wherein $A^1$ is a 5- to 7-membered saturated heterocyclic ring comprising the nitrogen atom which is attached to the quinoline ring and, wherein optionally a second nitrogen atom is present in the ring and, wherein the ring is optionally substituted by alkyl or amino.

Further preferred are compounds according to formula I, wherein $A^1$ is a 5- to 7-membered saturated heterocyclic ring comprising the nitrogen atom which is attached to the quinoline ring and, wherein optionally a second heteroatom is present in the ring which is selected from oxygen, sulfur or nitrogen and, wherein the second nitrogen atom which is optionally present is substituted by alkyl.

Another preferred aspect of the present invention are compounds according to formula I, wherein $A^1$ is a pyrrolidine, piperidine, azepane, piperazine or a [1,4]diazepane ring optionally substituted by alkyl, alkoxy, dialkylamino, or hydroxyalkyl. Particularly preferred are compounds according to formula I, wherein $A^1$ is a pyrrolidine, piperidine, azepane, piperazine or a [1,4]diazepane ring optionally substituted by alkyl, dimethylamino, or hydroxymethyl. Further preferred are compounds of formula I, wherein $A^1$ is a pyrrolidine, piperidine, azepane, piperazine, pyrrolidine or [1,4]diazepane ring optionally substituted by alkyl or amino. Very preferred are compounds of formula I, wherein $A^1$ is a pyrrolidine, piperidine, azepane, 4-methyl-piperazine, 3-dimethylamino-pyrrolidine or a 4-methyl[1,4]diazepane ring.

Further preferred are compounds of formula I, wherein $A^2$ is —$CH_2$—.

Another preferred embodiment of the present invention are compounds of formula I, wherein $A^2$ is —C(O)—.

Examples of preferred compounds of formula I are:
1. 3-(2-methyl-4-pyrrolidin-1-yl-quinolin-7-ylmethoxy)-benzonitrile;
2. (2-methyl-4-pyrrolidin-1-yl-quinolin-7-yl)-methanol;
3. (4-azepan-1-yl-2-methyl-quinolin-7-yl)-methanol;
4. 3-(4-azepan-1-yl-2-methyl-quinolin-7-ylmethoxy)-benzonitrile;
5. 4-(2-methyl-4-pyrrolidin-1-yl-quinolin-7-ylmethoxy)-benzonitrile;
6. 4-(4-azepan-1-yl-2-methyl-quinolin-7-ylmethoxy)-benzonitrile;
7. 2-methyl-4-pyrrolidin-1-yl-7-(3-trifluoromethyl-phenoxymethyl)-quinoline;
8. 2-methyl-4-pyrrolidin-1-yl-7-(4-trifluoromethyl-phenoxymethyl)-quinoline;
9. (2-methyl-4-pyrrolidin-1-yl-quinolin-7-ylmethyl)-(3-trifluoromethyl-phenyl)-amine;
10. 2-methyl-7-phenoxymethyl-4-pyrrolidin-1-yl-quinoline;
11. 4-azepan-1-yl-2-methyl-7-(3-trifluoromethyl-phenoxymethyl)-quinoline;
12. 7-(3-methoxy-phenoxymethyl)-2-methyl-4-pyrrolidin-1-yl-quinoline;
13. 4-[(2-methyl-4-pyrrolidin-1-yl-quinolin-7-ylmethyl)-amino]-benzonitrile;
14. 7-(2-methoxy-phenoxymethyl)-2-methyl-4-pyrrolidin-1-yl-quinoline;
15. 7-(2-fluoro-phenoxymethyl)-2-methyl-4-pyrrolidin-1-yl-quinoline;
16. 7-(3-fluoro-phenoxymethyl)-2-methyl-4-pyrrolidin-1-yl-quinoline;
17. 2-methyl-4-pyrrolidin-1-yl-7-o-tolyloxymethyl-quinoline;
18. 2-methyl-4-pyrrolidin-1-yl-7-m-tolyloxymethyl-quinoline;
19. 2-methyl-4-pyrrolidin-1-yl-7-p-tolyloxymethyl-quinoline;
20. 7-(4-fluoro-phenoxymethyl)-2-methyl-4-pyrrolidin-1-yl-quinoline;

21. [3-methoxy-4-(2-methyl-4-pyrrolidin-1-yl-quinolin-7-ylmethoxy)-phenyl]-pyrrolidin-1-yl-methanone;
22. 2-methyl-4-pyrrolidin-1-yl-quinoline-7-carboxylic acid amide;
23. 4-azepan-1-yl-7-methoxymethyl-2-methyl-quinoline;
24. 2-methyl-7-(pyridin-4-yloxymethyl)-4-pyrrolidin-1-yl-quinoline;
25. 4-azepan-1-yl-7-(2-methoxy-ethoxymethyl)-2-methyl-quinoline;
26. 7-(4-methoxy-phenoxymethyl)-2-methyl-4-pyrrolidin-1-yl-quinoline;
27. (2-methyl-4-pyrrolidin-1-yl-quinolin-7-yl)-pyrrolidin-1-yl-methanone;
28. 2-methyl-4-pyrrolidin-1-yl-quinoline-7-carboxylic acid (4-cyano-phenyl)-amide;
29. 2-methyl-4-pyrrolidin-1-yl-7-pyrrolidin-1-ylmethyl-quinoline;
30. 2-methyl-4-pyrrolidin-1-yl-quinoline-7-carboxylic acid butylamide;
31. 2-(2-methyl-4-pyrrolidin-1-yl-quinolin-7-ylmethoxy)-benzonitrile;
32. 2-chloro-4-(2-methyl-4-pyrrolidin-1-yl-quinolin-7-ylmethoxy)-benzonitrile;
33. 4-(2-methyl-4-pyrrolidin-1-yl-quinolin-7-ylmethoxy)-2-trifluoromethyl-benzonitrile;
34. butyl-(2-methyl-4-pyrrolidin-1-yl-quinolin-7-ylmethyl)-amine;
35. 2-fluoro-4-(2-methyl-4-pyrrolidin-1-yl-quinolin-7-ylmethoxy)-benzonitrile:
36. 4-fluoro-2-(2-methyl-4-pyrrolidin-1-yl-quinolin-7-ylmethoxy)-benzonitrile;
37. 3-fluoro-4-(2-methyl-4-pyrrolidin-1-yl-quinolin-7-ylmethoxy)-benzonitrile;
38. 3-chloro-4-(2-methyl-4-pyrrolidin-1-yl-quinolin-7-ylmethoxy)-benzonitrile;
39. 4-(2-methyl-4-pyrrolidin-1-yl-quinolin-7-ylmethoxy)-phthalonitrile;
40. 5-bromo-2-(2-methyl-4-pyrrolidin-1-yl-quinolin-7-ylmethoxy)-benzonitrile;
41. 4-(2-methyl-4-pyrrolidin-1-yl-quinolin-7-ylmethoxy)-2-nitro-benzonitrile;
42. 5-fluoro-2-(2-methyl-4-pyrrolidin-1-yl-quinolin-7-ylmethoxy)-benzonitrile;
43. 2-chloro-6-(2-methyl-4-pyrrolidin-1-yl-quinolin-7-ylmethoxy)-benzonitrile;
44. 3-fluoro-2-(2-methyl-4-pyrrolidin-1-yl-quinolin-7-ylmethoxy)-benzonitrile;
45. 2-iodo-6-(2-methyl-4-pyrrolidin-1-yl-quinolin-7-ylmethoxy)-benzonitrile;
46. 4-(2-methyl-4-pyrrolidin-1-yl-quinolin-7-ylmethoxy)-3-trifluoromethyl-benzonitrile;
47. 2-(2-methyl-4-pyrrolidin-1-yl-quinolin-7-ylmethoxy)-6-trifluoromethyl-benzonitrile;
48. 2-(2-methyl-4-pyrrolidin-1-yl-quinolin-7-ylmethoxy)-5-trifluoromethyl-benzonitrile;
49. 3,5-difluoro-2-(2-methyl-4-pyrrolidin-1-yl-quinolin-7-ylmethoxy)-benzonitrile;
50. 5-methyl-2-(2-methyl-4-pyrrolidin-1-yl-quinolin-7-ylmethoxy)-benzonitrile;
51. 4-bromo-2-(2-methyl-4-pyrrolidin-1-yl-quinolin-7-ylmethoxy)-benzonitrile;
52. 4-chloro-2-(2-methyl-4-pyrrolidin-1-yl-quinolin-7-ylmethoxy)-benzonitrile;
53. 3-fluoro-2-(2-methyl-4-pyrrolidin-1-yl-quinolin-7-ylmethoxy)-4-trifluoromethyl-benzonitrile;
54. 5-chloro-2-(2-methyl-4-pyrrolidin-1-yl-quinolin-7-ylmethoxy)-benzonitrile;
55. 4-[2-methyl-4-(4-methyl-piperazin-1-yl)-quinolin-7-ylmethoxy]-benzonitrile;
56. 2-(2-methyl-4-pyrrolidin-1-yl-quinolin-7-ylmethoxy)-4-trifluoromethyl-benzonitrile;
57. 4-(2-methyl-4-piperidin-1-yl-quinolin-7-ylmethoxy)-benzonitrile;
58. (S)-4-[4-(3-dimethylamino-pyrrolidin-1-yl)-2-methyl-quinolin-7-ylmethoxy]-benzonitrile;
59. 4-[2-methyl-4-(4-methyl-[1,4]diazepan-1-yl)-quinolin-7-ylmethoxy]-benzonitrile;
60. (2,6-Dimethyl-4-pyrrolidin-1-yl-quinolin-7-yl)-methanol;
61. 4-(2,6-Dimethyl-4-pyrrolidin-1-yl-quinolin-7-ylmethoxy)-benzonitrile;
62. 2-(2,6-Dimethyl-4-pyrrolidin-1-yl-quinolin-7-ylmethoxy)-benzonitrile;
63. {2-Methyl-4-[(S)-2-(tetrahydro-pyran-2-yloxymethyl)-pyrrolidin-1-yl]-quinolin-7-yl}-methanol;
64. 4-[(2-Methyl-4-pyrrolidin-1-yl-quinolin-7-ylmethyl)-amino]-2-trifluoromethyl-benzonitrile;
65. (S)-[1-(7-Hydroxymethyl-2-methyl-quinolin-4-yl)-pyrrolidin-2-yl]-methanol;
66. (S)-4-[4-(2-Hydroxymethyl-pyrrolidin-1-yl)-2-methyl-quinolin-7-ylmethoxy]-benzonitrile;
67. (S)-4-[4-(2-Hydroxymethyl-pyrrolidin-1-yl)-2-methyl-quinolin-7-ylmethoxy]-2-trifluoromethyl-benzonitrile;
68. (S)-4-[4-(2-Hydroxymethyl-pyrrolidin-1-yl)-2-methyl-quinolin-7-ylmethoxy]-3-trifluoromethyl-benzonitrile;
69. (S)-4-[4-(2-Hydroxymethyl-pyrrolidin-1-yl)-2-methyl-quinolin-7-ylmethoxy]-phthalonitrile;
70. (S)-2-[4-(2-Hydroxymethyl-pyrrolidin-1-yl)-2-methyl-quinolin-7-ylmethoxy]-benzonitrile;
71. 4-(2,6-Dimethyl-4-pyrrolidin-1-yl-quinolin-7-ylmethoxy)-2-trifluoromethyl-benzonitrile;
72. 4-(2,6-Dimethyl-4-pyrrolidin-1-yl-quinolin-7-ylmethoxy)-3-trifluoromethyl-benzonitrile;
73. (S)-[4-(2-Methoxymethyl-pyrrolidin-1-yl)-2,6-dimethyl-quinolin-7-yl]-methanol;
74. (R)-[4-(2-Methoxymethyl-pyrrolidin-1-yl)-2,6-dimethyl-quinolin-7-yl]-methanol;
75. (S)-4-[4-(2-Methoxymethyl-pyrrolidin-1-yl)-2,6-dimethyl-quinolin-7-ylmethoxy]-benzonitrile;
76. (R)-4-[4-(2-Methoxymethyl-pyrrolidin-1-yl)-2,6-dimethyl-quinolin-7-ylmethoxy]-benzonitrile;
77. (S)-[4-(3-Ethoxy-pyrrolidin-1-yl)-2,6-dimethyl-quinolin-7-yl]-methanol;
78. (S)-4-[4-(3-Ethoxy-pyrrolidin-1-yl)-2,6-dimethyl-quinolin-7-ylmethoxy]-benzonitrile;
79. (4-Azepan-1-yl-2,6-dimethyl-quinolin-7-yl)-methanol;
80. 4-[(2,6-Dimethyl-4-pyrrolidin-1-yl-quinolin-7-ylmethyl)-amino]-2-trifluoromethyl-benzonitrile;
81. (S)-1-(7-Hydroxymethyl-2,6-dimethyl-quinolin-4-yl)-pyrrolidin-3-ol;
82. (2-Chloro-6-methyl-4-pyrrolidin-1-yl-quinolin-7-yl)-methanol;
83. (4-Azepan-1-yl-2-chloro-6-methyl-quinolin-7-yl)-methanol;
84. (S)-4-[4-(3-Hydroxy-pyrrolidin-1-yl)-2,6-dimethyl-quinolin-7-ylmethoxy]-benzonitrile;
85. (S)-4-[4-(3-Methoxy-pyrrolidin-1-yl)-2,6-dimethyl-quinolin-7-ylmethoxy]-benzonitrile;
86. (S)-1-[2,6-Dimethyl-7-(tetrahydro-pyran-2-yloxymethyl)-quinolin-4-yl]-pyrrolidin-3-ol;
87. (S)-4-(3-Methoxy-pyrrolidin-1-yl)-2,6-dimethyl-7-(tetrahydro-pyran-2-yloxymethyl)-quinoline;
88. (6-Methoxy-2-methyl-4-pyrrolidin-1-yl-quinolin-7-yl)-methanol;

89. (6-Methyl-4-pyrrolidin-1-yl-quinolin-7-yl)-methanol;
90. (S)-[4-(3-Methoxy-pyrrolidin-1-yl)-2,6-dimethyl-quinolin-7-yl]-methanol;
91. 4-((S)-3-(Cyclopropylmethoxy)-pyrrolidin-1-yl)-2,6-dimethyl-7-(tetrahydro-pyran-2-yloxymethyl)-quinoline;
92. 4-Azepan-1-yl-2-chloro-6-methyl-7-(3-trifluoromethyl-phenoxymethyl)-quinoline;
93. (S)-4-{[4-(3-Ethoxy-pyrrolidin-1-yl)-2-methyl-quinolin-7-ylmethyl]-amino}-benzonitrile;
94. (S)-4-[4-(3-Ethoxy-pyrrolidin-1-yl)-2-methyl-quinolin-7-ylmethoxy]-benzonitrile;
95. (S)-[4-(3-(Cyclopropylmethoxy)-pyrrolidin-1-yl)-2,6-dimethyl-quinolin-7-yl]-methanol;
96. N-[4-Azepan-1-yl-6-methyl-7-(3-trifluoromethyl-phenoxymethyl)-quinolin-2-yl]-methyl-amine;
97. [4-Azepan-1-yl-6-methyl-7-(3-trifluoromethyl-phenoxymethyl)-quinolin-2-yl]-dimethyl-amine;
98. (4-Azepan-1-yl-2-dimethylamino-6-methyl-quinolin-7-yl)-methanol;
99. (S)-4-[4-(3-(Cyclopropylmethoxy)-pyrrolidin-1-yl)-2,6-dimethyl-quinolin-7-ylmethoxy]-benzonitrile;
100. 4-(6-Methyl-4-pyrrolidin-1-yl-quinolin-7-ylmethoxy)-benzonitrile;
101. 4-(4-Azepan-1-yl-2-dimethylamino-6-methyl-quinolin-7-ylmethoxy)-benzonitrile;
102. 4-[(2,6-Dimethyl-4-pyrrolidin-1-yl-quinolin-7-ylmethyl)-amino]-benzonitrile;
103. (S)-4-{[4-(3-Ethoxy-pyrrolidin-1-yl)-2,6-dimethyl-quinolin-7-ylmethyl]-amino}-benzonitrile;
104. 4-(6-Methyl-4-pyrrolidin-1-yl-quinolin-7-ylmethoxy)-2-trifluoromethyl-benzonitrile;
105. (S)-[4-(3-Ethoxy-pyrrolidin-1-yl)-6-methyl-quinolin-7-yl]-methanol;
106. (S)-4-{[4-(2-Hydroxymethyl-pyrrolidin-1-yl)-2,6-dimethyl-quinolin-7-ylmethyl]-amino}-benzonitrile;
107. 4-[(2,6-Dimethyl-4-pyrrolidin-1-yl-quinolin-7-ylmethyl)-methyl-amino]-benzonitrile;
108. (S)-4-[4-(3-Ethoxy-pyrrolidin-1-yl)-6-methyl-quinolin-7-ylmethoxy]-benzonitrile;
109. (S)-4-[4-(3-Ethoxy-pyrrolidin-1-yl)-6-methyl-quinolin-7-ylmethoxy]-2-trifluoromethyl-benzonitrile;
110. (S)-4-{[4-(3-Ethoxy-pyrrolidin-1-yl)-6-methyl-quinolin-7-ylmethyl]-amino}-2-trifluoromethyl-benzonitrile;
111. (S)-4-{[4-(3-Ethoxy-pyrrolidin-1-yl)-6-methyl-quinolin-7-ylmethyl]-amino}-benzonitrile;
112. 6-Bromo-2-methyl-4-pyrrolidin-1-yl-quinoline-7-carboxylic acid methyl ester; and
113. (6-Bromo-2-methyl-4-pyrrolidin-1-yl-quinolin-7-yl)-methanol.

Examples of particularly preferred compounds of formula I are:

(4-azepan-1-yl-2-methyl-quinolin-7-yl)-methanol;
4-(2-methyl-4-pyrrolidin-1-yl-quinolin-7-ylmethoxy)-benzonitrile;
4-(4-azepan-1-yl-2-methyl-quinolin-7-ylmethoxy)-benzonitrile;
4-[(2-methyl-4-pyrrolidin-1-yl-quinolin-7-ylmethyl)-amino]-benzonitrile;
2-methyl-7-(pyridin-4-yloxymethyl)-4-pyrrolidin-1-yl-quinoline;
2-methyl-4-pyrrolidin-1-yl-quinoline-7-carboxylic acid butylamide;
2-(2-methyl-4-pyrrolidin-1-yl-quinolin-7-ylmethoxy)-benzonitrile;
2-chloro-4-(2-methyl-4-pyrrolidin-1-yl-quinolin-7-ylmethoxy)-benzonitrile;
4-(2-methyl-4-pyrrolidin-1-yl-quinolin-7-ylmethoxy)-2-trifluoromethyl-benzonitrile;
4-(2-methyl-4-pyrrolidin-1-yl-quinolin-7-ylmethoxy)-phthalonitrile;
(2,6-Dimethyl-4-pyrrolidin-1-yl-quinolin-7-yl)-methanol;
4-(2,6-Dimethyl-4-pyrrolidin-1-yl-quinolin-7-ylmethoxy)-benzonitrile;
4-[(2-Methyl-4-pyrrolidin-1-yl-quinolin-7-ylmethyl)-amino]-2-trifluoromethyl-benzonitrile;
(S)-[4-(3-Ethoxy-pyrrolidin-1-yl)-2,6-dimethyl-quinolin-7-yl]-methanol;
(S)-4-[4-(3-Ethoxy-pyrrolidin-1-yl)-2,6-dimethyl-quinolin-7-ylmethoxy]-benzonitrile;
4-[(2,6-Dimethyl-4-pyrrolidin-1-yl-quinolin-7-ylmethyl)-amino]-benzonitrile; and
(S)-4-{[4-(3-Ethoxy-pyrrolidin-1-yl)-2,6-dimethyl-quinolin-7-ylmethyl]-amino}-benzonitrile.

Processes for the manufacture of compounds of formula I are an object of the invention.

The substituents and indices used in the following description of the processes have the significance given above unless indicated to the contrary.

Compounds of general formula IA ($R^1$=$OR^4$, $A^2$=$CH_2$) can be prepared according to scheme 1 in two steps from (4-chloroquinolin-7-yl)methanol derivative A as follows:

a) For the conversion of A into (7-quinolylmethyl) ether B, A is reacted with a phenol derivative, $R^{41}$—OH ($R^{41}$=aryl, heterocyclyl), in the presence of triphenylphosphine and a dialkyl azodicarboxylate (e.g., diisopropyl azodicarboxylate) in a non-protic solvent such as dichloromethane or toluene at about room temperature (Mitsunobu-reaction, for a review see *Org. React.* 1992, 42, 335). Alternatively, A is treated with $R^{41}$—X ($R^{41}$ is aryl or heterocyclyl and X is halogen, preferably F) or $R^{42}$—Y ($R^{42}$ is alkyl or cycloalkyl; Y is a leaving group, preferably Br or I) in the presence of a base, e.g., sodium hydride, in a solvent such as N,N-dimethylformamide, at temperatures between 20–100° C. Alternatively, the transformation of A into B is accomplished by cross-coupling reaction with an halide $R^{41}$—X ($R^{41}$ is aryl or heterocyclyl; X is hal, preferably Br or I), in the presence of a base, e.g., sodium hydride or sodium tert-butylate, and a palladium catalyst system, e.g., tris(dibenzylideneacetone)dipalladium(0) and 2,2'-bis(di-p-tolylphosphino)-1,1'-binaphthyl (Tol-BINAP), in a solvent such as toluene, at about 50–100° C. (*J. Am. Chem. Soc.* 1997, 119, 3395).

b) The conversion of (4-chloroquinolin-7-yl)methyl ether B to compound IA is accomplished with an appropriate amine at temperatures between 0–200° C. optionally in a sealed tube and/or under microwave irradiation, either using a large excess of the amine without solvent, or on reaction with a 2–20-fold excess, in a suited solvent such as ethanol or 1-methylpyrrolidin-2-one, optionally in the presence of lithium chloride or sodium iodide and pyridine. In the case of $R^{30}$=halogen, the isomeric 2-aminoquinoline derivative, which may result as a side product, is separated from the desired 4-aminoquinoline, e.g., by chromatography or crystallization.

Alternatively, the conversion (4-chloroquinolin-7-yl) methanol derivative A to IA can be accomplished via IB, by inverting the order of the reaction steps described above (scheme 1).

Scheme 1

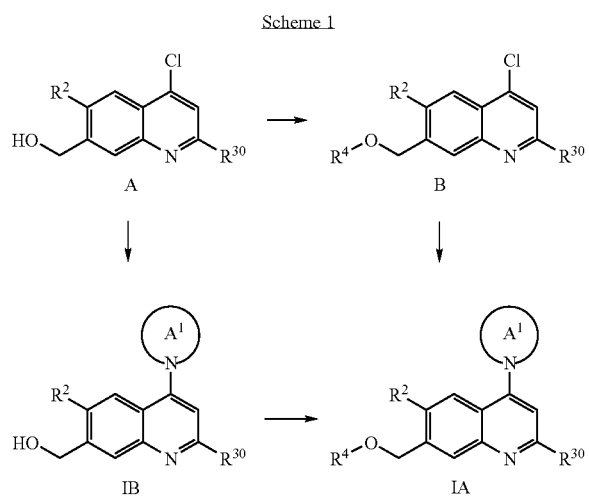

$R^{30}$ is H, alkyl or halogen;

The synthesis of (4-chloroquinolin-7-yl)methanol derivative A from 4-chloroquinoline C is outlined in scheme 2.

a) Cross-coupling reaction of C with a metal cyanide, e.g., potassium cyanide, in the presence of a palladium catalyst, e.g., tetrakis(triphenylphosphine)palladium(0) and copper(I)iodide, in a solvent such as acetonitrile, at 80° C. (*J. Org. Chem.* 1998, 63, 8224), produces 4-chloroquinoline-7-carbonitrile D.

b) Alcoholysis of the cyano group of D, preferably in ethanolic or methanolic hydrogen chloride solution, at temperatures between 20° C. and the boiling point of the alcohol, affords 4-chloroquinoline-7-carboxylic ester E.

c) Hydride reduction of E with a suited reagent, preferably with diisobutylaluminum hydride, in a solvent such as THF or dichloromethane, at temperatures between −78° C. and +20° C., yields (4-chloroquinolin-7-yl)methanol A.

Alternatively, A is obtained from D by a two-step sequence, in which the cyano group of D is reduced with diisobutylaluminum hydride, in a solvent such as tetrahydrofuran, at temperatures between −78° C. and 0° C., and the 4-chloroquinoline-7-carbaldehyde (F) obtained is treated with sodium borohydride in a solvent such as methanol, at 0–20° C.

Alternatively, a one-step conversion of C into E is accomplished by carbonylation, i.e., by reacting halide or triflate C with an appropriate alcohol ($R^a$—OH, where $R^a$ is lower alkyl, preferably methyl or ethyl), either using a large excess of the alcohol without solvent, or on reaction with a 2–10-fold excess, in a suited solvent such as N,N-dimethylformamide or methyl sulfoxide, under a carbon monoxide atmosphere at pressures between 1 and 100 bar, in the presence of a palladium catalyst system, e.g., palladium(II)acetate and triphenyl phosphine or bis(1,3-diphenylphosphino)propane, and a base, e.g., triethylamine, at about 40–80° C.

Scheme 2

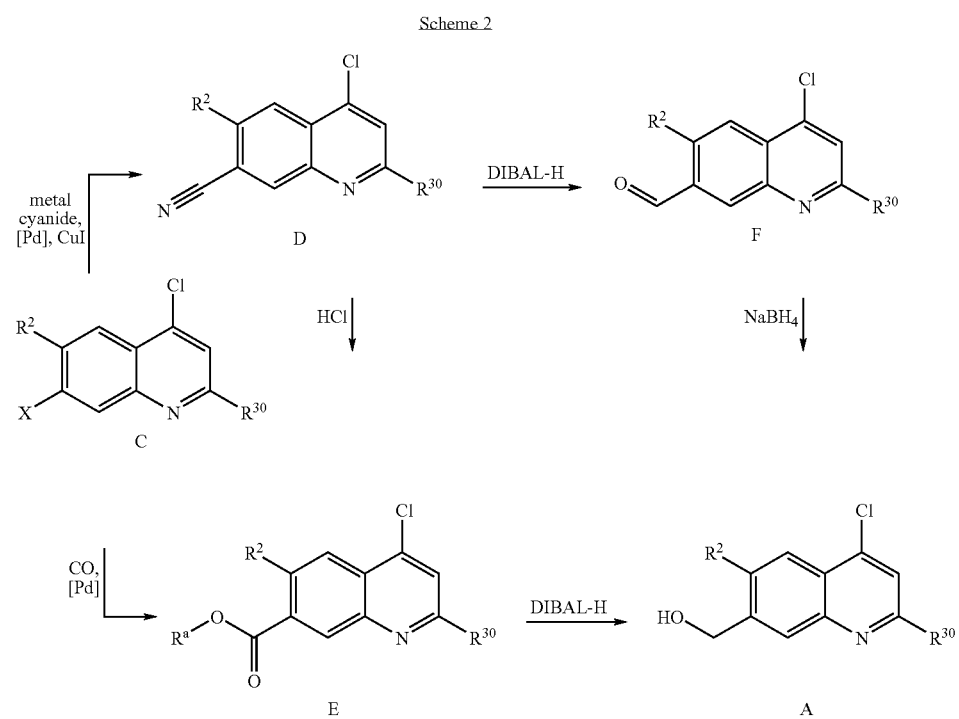

$R^{30}$ is hydrogen, alkyl or halogen; $R^a$ is methyl or ethyl; X is a leaving group, preferably I or $OSO_2CF_3$.

The synthesis of quinoline-7-carboxamide compounds of the general formula IC from from 4-chloro-7-haloquinoline C is outlined in scheme 3:

a) The reaction of C with appropriate amines to produce G is performed in analogy to the synthesis of IA from B as described above.
b) 4-Aminoquinoline-7-carbonitrile derivative H is produced from G by cross-coupling reaction with a metal cyanide, in analogy to the transformation of C into D, as described above.
c) Hydrolysis of H, e.g., with hydrogen peroxide and potassium hydroxide, preferably in a two-phase mixture of water and dichloromethane and in the presence of a phase-transfer catalyst, e.g., tetrabutylammonium hydrogen sulfate, at a temperature of 0–20° C., yields primary amide ID.
d) Finally, the conversion of ID into IC is performed, either by reaction with a halide or sulfonate, $R^{42}$—Y ($R^{42}$= (substituted) alkyl or cycloalkyl, Y=leaving group, preferably Br or I), in the presence of a base, e.g., sodium hydride, in a solvent such as N,N-dimethylformamide, at temperatures between 20–100° C., or by cross-coupling reaction with a halide, $R^{41}$—X ($R^{41}$=aryl, heterocyclyl, X=halogen, preferably Br or I), in the presence of a base, e.g., cesium carbonate, and a palladium catalyst system, e.g., palladium(II)acetate and 4,5-bis(diphenylphosphino)-9,9-dimethylxanthene (Xantphos), in a solvent such as 1,4-dioxane, at about 50–100° C. (*Org. Lett.* 2000, 2, 1101).

Scheme 3

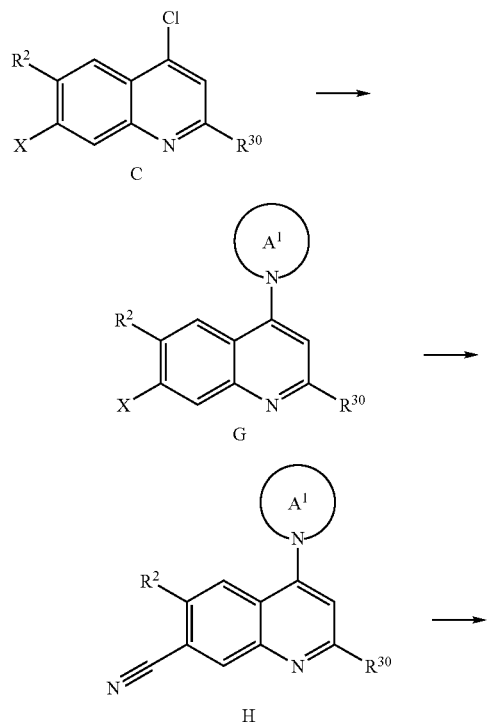

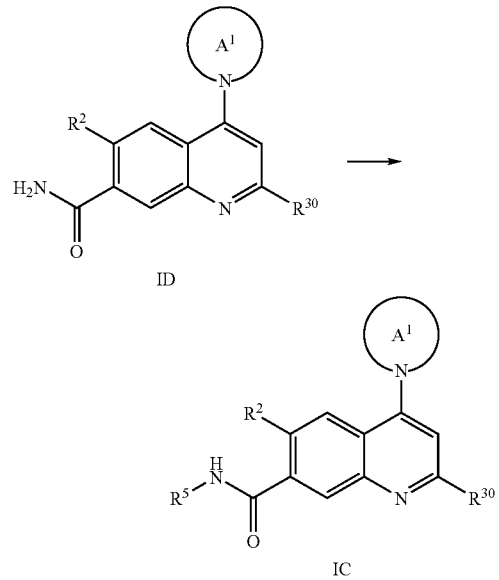

$R^{30}$ is hydrogen, alkyl or halogen; X is a leaving group, preferably I or $OSO_2CF_3$.

The synthesis of 4-aminoquinoline-7-carboxamide derivatives IE and (4-aminoquinolin-7-ylmethyl)amines IF is outlined in scheme 4:

a) Ester E is converted into the corresponding amide J by reaction with an appropriate amine, either using a large excess of the amine without solvent, or on reaction with a 2–10-fold excess of the amine, in a suited solvent such as ethanol or N,N-dimethylformamide, at temperatures between 0° C. and the boiling point of the amine or solvent.
b) The reaction of J with appropriate amines to produce IE is performed in analogy to the synthesis of IA from B as described above.
c) The conversion of IE into IF is accomplished by hydride reduction, e.g., with lithium aluminumhydride in a solvent such as tetrahydrofuran, at temperatures between 0° C. and the boiling point of the solvent.

Scheme 4

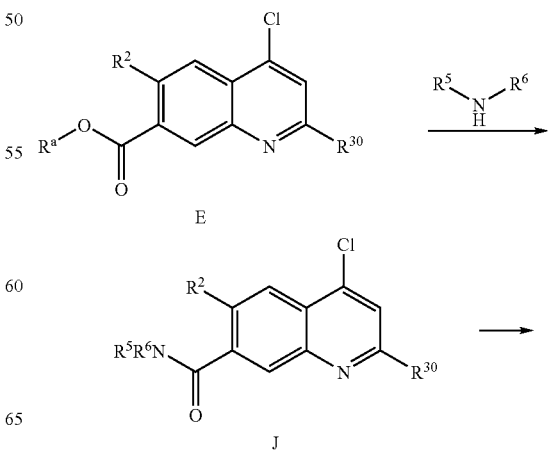

-continued

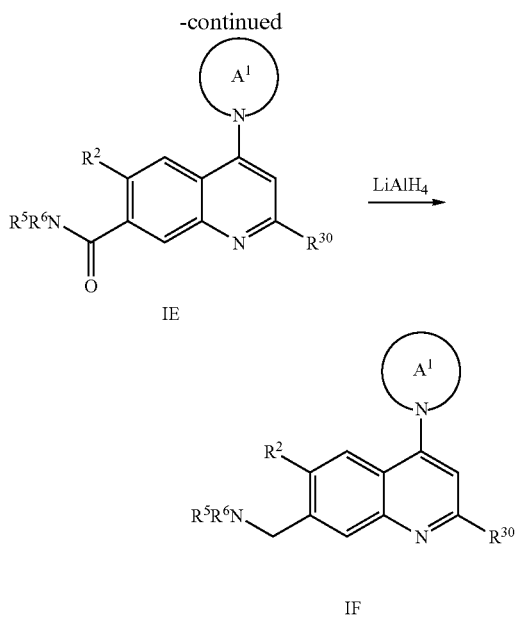

$R^{30}$ is hydrogen, alkyl or halogen; $R^a$ is methyl or ethyl.

An alternative entry to compounds IF (especially preferred in the case of $R^5$=aryl or heterocyclyl) is outlined in scheme 5:

a) Oxidation of (4-chloroquinolin-7-yl)methanol A with manganese dioxide in a solvent such as dichloromethane or chloroform, at temperatures between 20° C. and the boiling point of the solvent, affords quinoline-7-carbaldehyde derivative F.

b) Reductive amination of F, using an appropriate amine and a borohydride reagent, e.g., sodium borohydride or sodium triacetoxyborohydride, in a solvent system such as ethanol/acetic acid, ethanol/aq. hydrochloric acid, or 1,2-dichloroethane/acetic acid, at 0–20° C., affords (4-chloroquinolin-7-yl)methylamine K.

c) The reaction of K with appropriate amines to produce IF is performed in analogy to the synthesis of IA from B as described above.

Alternatively, IF may be synthesized from alcohol IB by oxidation with manganese dioxide (according to step a), followed by reductive amination (according to step b)

Scheme 5

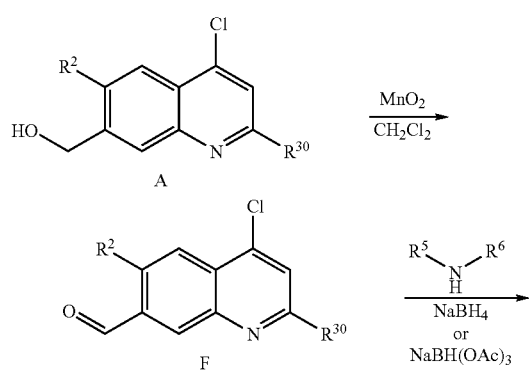

-continued

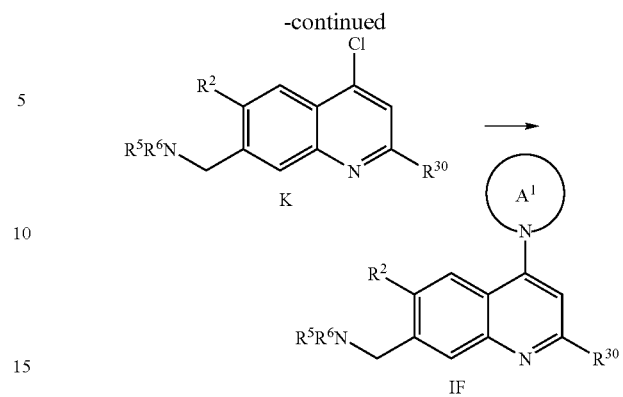

$R^{30}$ is hydrogen, alkyl or halogen.

Quinoline derivatives IH ($R^{20}$=amino, alkoxy) can be prepared from 6-haloquinoline derivatives IG, by cross-coupling reaction with appropriate amines ($R^5$—NH—$R^6$) or alcohols ($R^{43}$—OH), in the presence of a catalyst system and a base as follows (scheme 6):

a) In the case of $R^{20}$=alkoxy, the cross-coupling reaction is performed either by the Ullmann method, using a copper catalyst system, e.g., copper iodide with or without 1,10-phenanthroline, and a base, e.g., sodium tert-butylate or cesium carbonate, in the alcohol, $R^{43}$—OH, as the solvent, or in a solvent such as N,N-dimethylformamide and at elevated temperatures (*Synthesis* 1998, 1599 or *Org. Lett.* 2002, 4, 973), or by the Buchwald method, using a palladium catalyst system, e.g., tris(dibenzylideneacetone)dipalladium(0) and 2,2'-bis(di-p-tolylphosphino)-1,1'-binaphthyl (Tol-BINAP), in a solvent such as toluene, at about 50–100° C. (*J. Am. Chem. Soc.* 1997, 119, 3395).

b) In the case of $R^{20}$=amino, the conversion is accomplished by Buchwald cross-coupling reaction in the presence of a suited catalyst system such as palladium(II)acetate and 2,2'-bis(diphenylphosphino)-1,1'-binaphthyl (BINAP) and a base, e.g., sodium tert-butylate, in a solvent such as toluene, at 20–110° C. (*J. Org. Chem.* 1996, 61, 7240).

Scheme 6

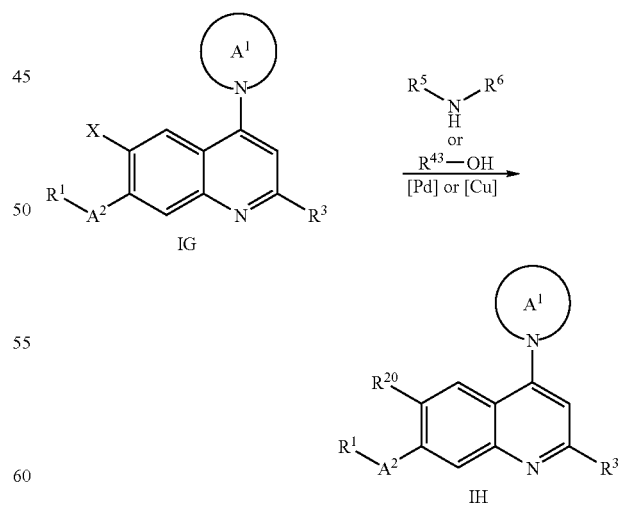

$R^{20}$ is alkoxy or amino; X is Cl, Br or I; $R^{43}$ is alkyl.

Quinoline derivatives IK can be prepared from 2-chloroquinoline derivatives IJ and appropriate amines, according to scheme 7, either in analogy to the synthesis of IA from B, or by Buchwald cross-coupling reaction, in analogy to the synthesis of IH from IG, as described above.

Scheme 7

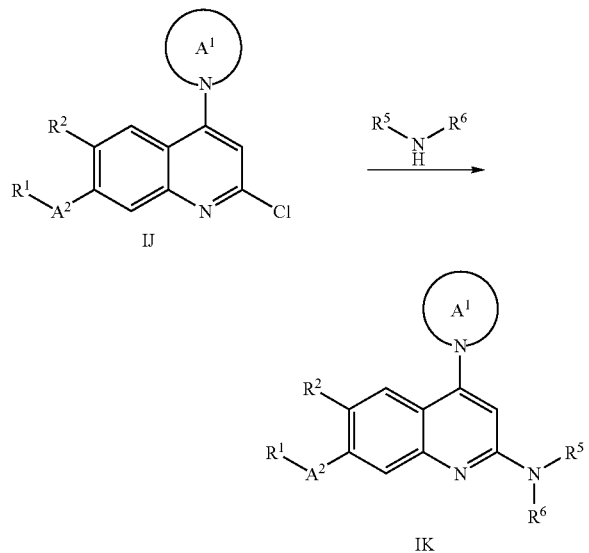

Quinoline-7-carboxylic acid ester derivatives of general formula IL can be prepared from compounds G by carbonylation, in analogy to the synthesis of C to E, as described above. Esters IL can then be converted to alcohols IB by hydride reduction in analogy to the synthesis of E to A, as described above.

Scheme 8

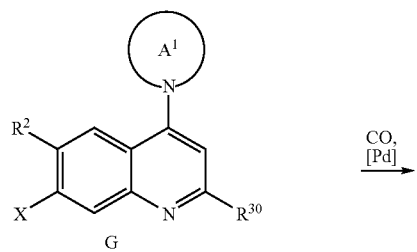

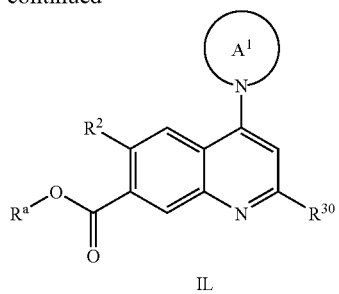

IL $R^{30}$ is hydrogen, alkyl or halogen; $R^a$ is methyl or ethyl; X is a leaving group, preferably I or $OSO_2CF_3$.

The preparation of 4-chloroquinolines C is depicted in schemes 9 and 10 and involves the elaboration of 3-haloanilines or 3-benzyloxyanilines of formula L according to methods known in the art (for a general review see G. Jones, 'The chemistry of heterocyclic compounds, vol. 32: Quiniolines', Part I, J. Wiley and Sons, London, 1977). For the preparation of 4-chloroquinolines according to formula C1, 3-haloanilines or 3-benzyloxyanilines (L) are transformed as follows, depending on the nature of the substituent $R^c$ at C(2) of the quinoline:

a) $R^c$=H: Condensation with a dialkyl ethoxy methylenemalonate at 140–150° C. produces intermediate M1, which is cyclized under elimination of one equivalent of alcohol ($R^a$—OH) on heating at about 250° C. in a high boiling solvent such as Dowtherm® A or diphenyl ether. The 4-quinolone-3-carboxylic ester thus obtained is saponified (aqueous sodium hydroxide, reflux) and decarboxylated under thermal conditions (ca. 250° C.) in a solvent such as Dowtherm® A or diphenyl ether to give 4-quinolone N1 (scheme 9).

b) $R^c$=alkyl: Condensation with appriopriate β-ketoesters in the presence of p-toluenesulfonic acid, in refluxing cyclohexane and under azeotropic removal of the water produced during the reaction, affords intermediate M2. Subsequent ring closure under elimination of one equivalent of alcohol ($R^a$—OH) is achieved on heating at about 250° C. in a high boiling solvent such as Dowtherm® A to give 4-quinolone N1 (scheme 9).

The conversion of the quinolones N1 thus produced into 4-chloroquinolines C1 is accomplished, e.g., with phosphorus oxide chloride and, optionally, in the presence of catalytic amounts of N,N-dimethylformamide, at about 50° C. (scheme 9).

Scheme 9

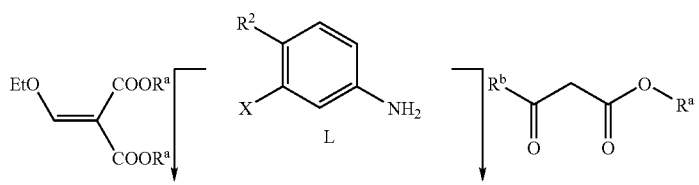

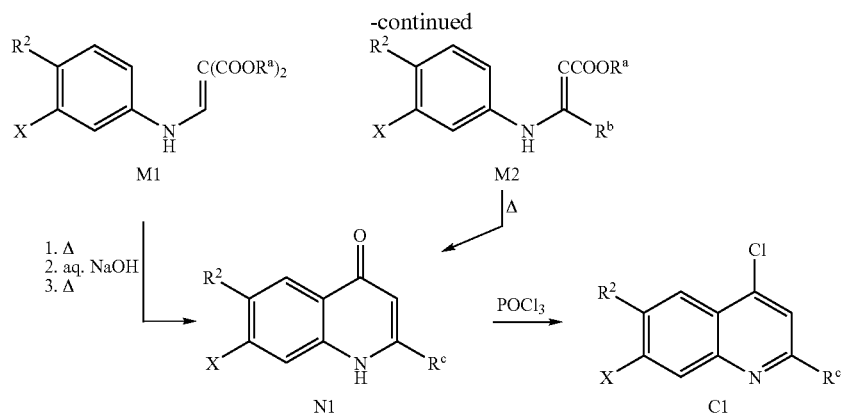

$R^a$ is methyl or ethyl; $R^b$ is alkyl; $R^c$ is H or alkyl; X is I, $OCH_2Ph$ or Br, preferably I or $OCH_2Ph$.

For the preparation of 2,4-dichloroquinolines of formula C2, two equivalents of 3-haloaniline or 3-benzyloxyaniline (L) are condensed with one equivalent of a dialkylmalonate at a high temperature (ca. 210° C.) and under continuous removal of the two equivalents of alcohol ($R^a$—OH) released. The dianilide intermediate M3 is cyclized on heating at about 250° C. in a melt of aluminum chloride and sodium chloride to provide the 4-hydroxy-2-quinolone of the general formula N2. Finally, chlorination with $POCl_3$ produces the 2,4-dichloroquinolines C2 (scheme 10).

Alternatively, 2,4-dichloroquinolines C2 can be synthesized in one step from anilines L, malonic acid, and $POCl_3$ (*J. Chem. Soc., Perkin Trans* 1 1993, 2747).

Scheme 10

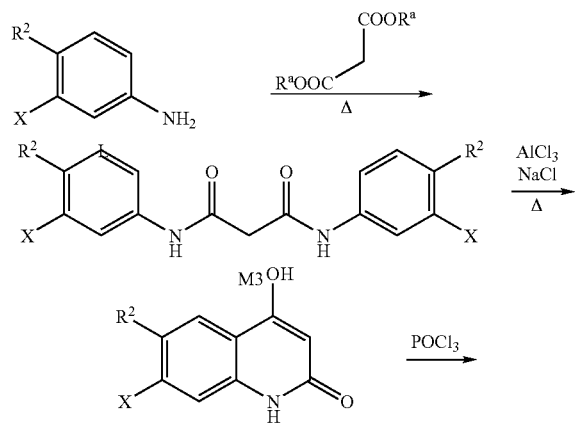

$R^a$ is methyl or ethyl, X is I, $OCH_2Ph$ or Br, preferably I or $OCH_2Ph$.

Quinoline derivatives C3 or G1, having a benzyloxy group at the C(7) position, can be converted to the corresponding quinolin-7-yl triflates C4 and G2, respectively, via a two-step sequence outlined in scheme 11:

a) The benzyl ether moiety in C3 or G1 moiety is cleaved, e.g., either using a Lewis acid (preferably titanium(IV) chloride in dichloromethane, at about 0° C.) or reductively (by hydrogenation in the presence of a suitable catalyst, e.g., palladium on activated charcoal, in a solvent such as methanol), to afford the corresponding quinolin-7-ol.

b) The quinolin-7-ol intermediates are converted into the corresponding triflates C4 or G2 using a suited reagent, e.g., trifluoromethanesulfonic anhydride, in a solvent such as dichloromethane, at about −20° C.

The reaction of C3 with appropriate amines to produce G1 is performed in analogy to the synthesis of IA from B as described above.

Scheme 11

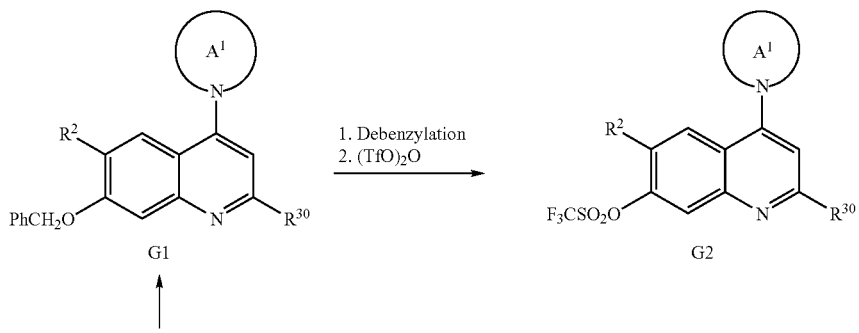

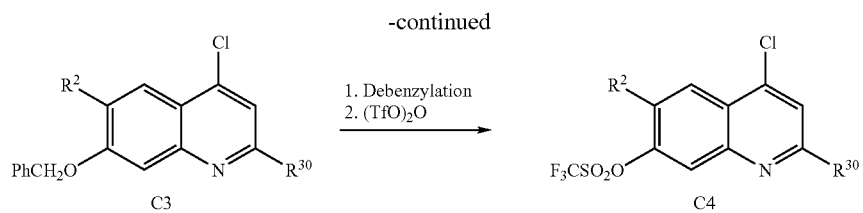

$R^{30}$ is hydrogen, alkyl or halogen.

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid.

The conversion of compounds of formula I into pharmaceutically usable esters or amides can be carried out e.g. by treatment of suited amino or hydroxyl groups present in the molecules with an carboxylic acid such as acetic acid, with a condensating reagent such as benzotriazol-1-yloxytris (dimethylamino)phosphonium hexafluorophosphate (BOP) or N,N-dicylohexylcarbodiimide (DCC) to produce the carboxylic ester or carboxylic amide.

Preferred intermediates are:
a) 4-chloro-2-methyl-quinoline-7-carboxylic acid ethyl ester;
b) (4-chloro-2-methyl-quinolin-7-yl)-methanol;
c) 4-chloro-2-methyl-quinoline-7-carbaldehyde;
d) 2-methyl-4-pyrrolidin-1-yl-quinoline-7-carbonitrile;
e) 4-chloro-2,6-dimethyl-quinoline-7-carboxylic acid ethyl ester;
f) 2,6-dimethyl-4-pyrrolidin-1-yl-quinoline-7-carbaldehyde;
g) 2,4-dichloro-7-iodo-6-methyl-quinoline;
h) 2,4-dichloro-6-methyl-quinoline-7-carboxylic acid ethyl ester;
i) (4-chloro-6-methoxy-2-methyl-quinolin-7-yl)-methanol;
j) (4-chloro-6-methyl-quinolin-7-yl)-methanol;
k) 4-chloro-2,6-dimethyl-quinoline-7-carbaldehyde;
l) 7-benzyloxy-6-bromo-4-chloro-2-methyl-quinoline;
m) trifluoro-methanesulfonic acid 6-bromo-2-methyl-4-pyrrolidin-1-yl-quinolin-7-yl ester.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions containing a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

A preferred process for the preparation of a compound of formula I comprises one of the following reactions:
a) a compound of formula Q1 is reacted in the presence of an amine of the formula Q2 in order to obtain a compound according to formula Q3

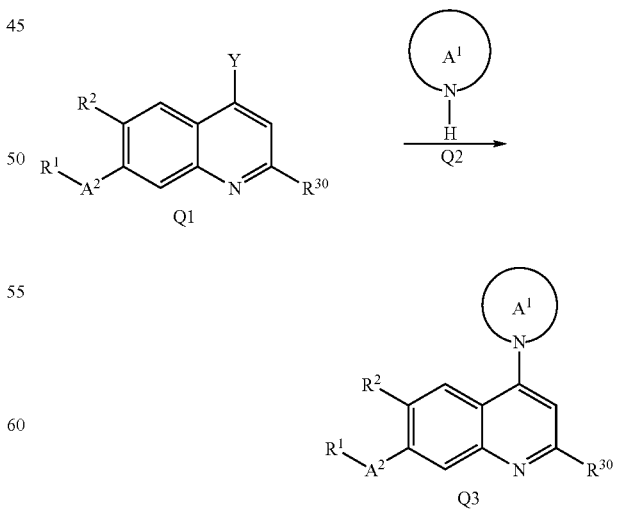

wherein $R^1$, $R^2$, $A^1$ and $A^2$ are defined as above and $R^{30}$ is hydrogen, alkyl or halogen and Y is chloro, bromo or iodo;

b) a compound of formula H is reacted in the presence of hydrogen peroxide in order to obtain a compound according to formula ID

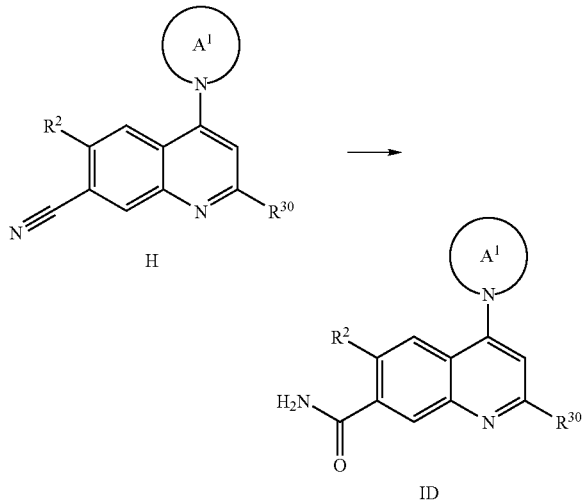

wherein $R^2$ and $A^1$ are defined as above in claim 1 and $R^{30}$ is hydrogen, alkyl or halogen;

c) a compound according to formula IE is reacted in the presence of a hydride in order to obtain a compound according to formula IF

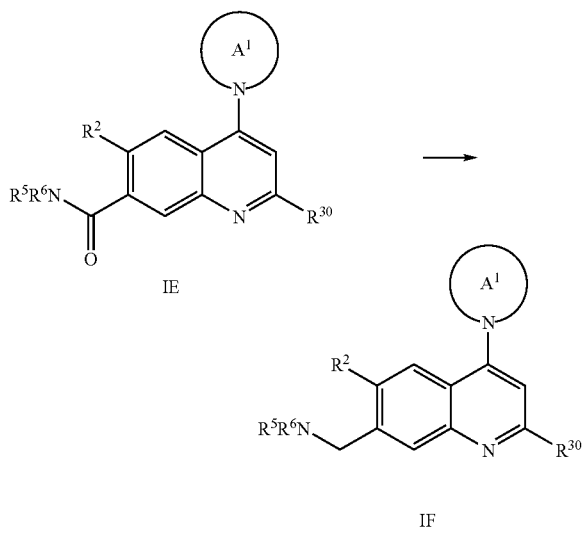

wherein $R^2$, $R^5$, $R^6$ and $A^1$ are defined as above and wherein $R^{30}$ is hydrogen, alkyl or halogen;

d) a compound according to formula IJ is reacted in the presence of a corresponding amine HNR'R'' in order to obtain a compound of formula IK

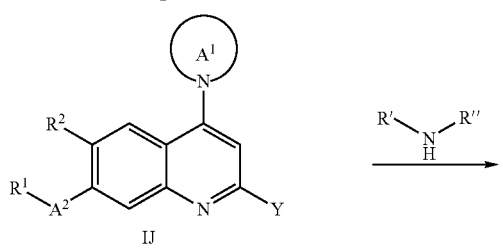

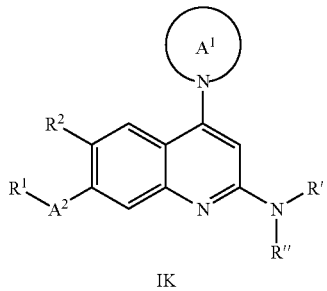

wherein $R^1$, $R^2$, $A^1$ and $A^2$ are defined as above and R' and R" are independently selected from hydrogen, alkyl and cycloalkyl or R' and R" together with the N atom to which they are attached form a 5- to 10-membered heterocyclic ring wherein the heterocyclyc ring is optionally substituted with one or more substituents independently selected from alkyl and alkoxy and Y is chloro, bromo or iodo.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention is a pharmaceutical composition comprising a compound of formula I described above and a therapeutically inert carrier. Preferred is this composition comprising further a therapeutically effective amount of a lipase inhibitor. Particularly preferred is the above composition, wherein the lipase inhibitor is orlistat.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Assay Procedures

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase (Stratagene). The amplification product was subcloned into the mammalian expression vector pcDNA3 using Eco RI and XhoI restriction sites. Positive clones were sequenced and one clone, encoding the published sequence was selected for generation of stable cell clones.

Stable Transfection

Human embryonic kidney 293 (HEK293) cells were transfected with 10 μg mNPY5 DNA using the lipofectamine reagent (Gibco BRL) according to the manufacturer's instruction. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labelled peptide YY (PYY) and 10 μL DMSO containing increasing amounts of unlabelled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I] labelled neuropeptide Y. It is determined by linear regression analysis after logit/log transformation of the binding data.

Results obtained in the foregoing test using representative compounds of the invention as the test compounds are shown in the following table:

| Compound | $IC_{50}$ |
|---|---|
| Example 5 | 22 nM |
| Example 13 | 130 nM |

Preferred compounds as described above have $IC_{50}$ values below 1000 nM; more preferred compounds have $IC_{50}$ values below 100 nM. Most preferred compounds have $IC_{50}$ values below 10 nM. These results have been obtained by using the foregoing test.

The compounds of formula I and their pharmaceutically usable salts, solvates and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically usable salts, solvates and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts, solvates and esters can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by the examples, which have no limiting character.

EXAMPLES

Example 1

3-(2-Methyl-4-pyrrolidin-1-yl-quinolin-7-yl-methoxy)-benzonitrile

The title compound was produced in accordance with the general method of example 20 from (4-chloro-2-methyl-quinolin-7-yl)-methanol (example 2c), 3-hydroxybenzonitrile, and pyrrolidine. Yellow solid, ISP-MS: m/e=344.4 ([M+H]$^+$).

Example 2

(2-Methyl-4-pyrrolidin-1-yl-quinolin-7-yl)-methanol a) 4-Chloro-2-methyl-quinoline-7-carbonitrile The title compound was produced in accordance with the general method of example 22b from 4-chloro-7-iodo-2-methyl-quinoline (EP497371). White solid, ISP-MS: m/e=203.0 ([M+H]$^+$).

b) 4-Chloro-2-methyl-quinoline-7-carboxylic acid ethyl ester

Method A: A suspension of 4-chloro-2-methyl-quinoline-7-carbonitrile (52 mg, 0.26 mmol) in 8 M ethanolic hydrogen chloride solution (4 mL) was heated at 80° C. for 2 h. After cooling the solution obtained was poured onto saturated sodium hydrogencarbonate solution and extracted with ethyl acetate. The organic layer was washed with brine, dried (MgSO$_4$), and evaporated to yield the title compound (51 mg, 80%). White solid, ISP-MS: m/e=250.1 ([M+H]$^+$).

Method B: A mixture of 4-chloro-7-iodo-2-methyl-quinoline (EP497371, 20.0 g, 65.9 mmol), palladium(II)acetate (740 mg, 3.30 mmol), triphenylphosphine (864 mg, 3.30 mmol) and triethylamine (20.0 g, 198 mmol) in ethanol (400 mL) was heated under a carbon monoxide atmosphere at 55° C. for 13 h. After cooling the solution obtained was partitioned between sat. aq. ammonium chloride solution and ethyl acetate, the organic layer was washed with sat. aq. ammonium chloride solution and brine, dried (MgSO$_4$) and evaporated to afford the title compound (16.9 g) which was used without further purification. Light yellow solid.

c) (4-Chloro-2-methyl-quinolin-7-yl)-methanol

Diisobutylaluminum hydride (1 M solution in tetrahydrofuran, 80 mL, 80 mmol) was added dropwise at 0° C. to a solution of 4-chloro-2-methyl-quinoline-7-carboxylic acid ethyl ester (4.42 g, 17.7 mmol) in tetrahydrofuran (90 mL), then after stirring 1 h at 0° C. the reaction was quenched by careful addition of methanol (4.5 mL) and 1 M aq. potassium sodium tartrate solution (135 mL). The two-phase mixture was stirred 30 min, then extracted twice with ethyl acetate. The organic phases were washed with brine, dried (MgSO$_4$) and evaporated. Chromatography (SiO$_2$, hexane/ethyl acetate 1:1 afforded the title compound (2.62 g, 71%). Off-white solid, EI-MS: m/e=207.2 (M$^+$).

d) (2-Methyl-4-pyrrolidin-1-yl-quinolin-7-yl)-methanol (4-Chloro-2-methyl-quinolin-7-yl)-methanol (750 mg, 3.61 mmol) was refluxed in pyrrolidine (6.42 g, 90.3 mmol) for 16 h. Most of the pyrrolidine was then removed under reduced pressure, the oily residue was taken up in toluene, evaporated, and the solid obtained triturated in ethyl acetate, filtered and dried to afford the title compound (785 mg, 90%). Light brown solid, ISP-MS: m/e=243.3 ([M+H]$^+$).

Example 3

(4-Azepan-1-yl-2-methyl-quinolin-7-yl)-methanol (4-Chloro-2-methyl-quinolin-7-yl)-methanol (example 2c, 1.00 g, 4.82 mmol) was heated at 125° C. in azepane (8.79 g, 90.3 mmol) for 18 h. After cooling the reaction mixture was partitioned between sat. aq. ammonium chloride solution and ethyl acetate. The organic layer was separated, washed with brine, dried (MgSO$_4$), and evaporated. Chromatography on SiO$_2$ (ethyl acetate, then CH$_2$Cl$_2$/MeOH/NH$_4$OH 95:5:0.1) yielded the title compound (320 mg, 25%). Light yellow solid, ISP-MS: m/e=271.4 ([M+H]$^+$).

Example 4

3-(4-Azepan-1-yl-2-methyl-quinolin-7-ylmethoxy)-benzonitrile

The title compound was produced in accordance with the general method of example 20 from (4-chloro-2-methyl-quinolin-7-yl)-methanol (example 2c), 3-hydroxybenzonitrile, and azepane. Light yellow solid, ISP-MS: m/e=372.3 ([M+H]$^+$).

Example 5

4-(2-Methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 4-fluorobenzonitrile. White solid, ISP-MS: m/e=344.3 ([M+H]$^+$).

Example 6

4-(4-Azepan-1-yl-2-methyl-quinolin-7-ylmethoxy)-benzonitrile

Sodium hydride (55–65% dispersion in mineral oil, 22 mg, 0.55 mmol) was added to a mixture of (4-azepan-1-yl-2-methyl-quinolin-7-yl)-methanol (example 3, 120 mg, 0.44 mmol) and 4-fluorobenzonitrile (54 mg, 0.44 mmol) in N,N-dimethylformamide (1.5 mL). After heating 2 h at 50° C., the reaction mixture was partitioned between sat. aq. ammonium chloride solution and dichloromethane. The organic layer was separated, washed with brine, dried (MgSO$_4$), and evaporated. Chromatography (SiO$_2$, CH$_2$Cl$_2$/MeOH 95:5) yielded the title compound (144 mg, 87%). Light yellow solid, ISP-MS: m/e=372.3 ([M+H]$^+$).

Example 7

2-Methyl-4-pyrrolidin-1-yl-7-(3-trifluoromethyl-phenoxymethyl)-quinoline

The title compound was produced in accordance with the general method of example 20 from (4-chloro-2-methyl-quinolin-7-yl)-methanol (example 2c), 3-trifluoromethylphenol, and pyrrolidine. Light brown solid, ISP-MS: m/e=387.3 ([M+H]$^+$).

Example 8

2-Methyl-4-pyrrolidin-1-yl-7-(4-trifluoromethyl-phenoxymethyl)-quinoline

The title compound was produced in accordance with the general method of example 20 from (4-chloro-2-methyl-quinolin-7-yl)-methanol (example 2c), 4-trifluoromethylphenol, and pyrrolidine. Light brown solid, ISP-MS: m/e=387.3 ([M+H]$^+$).

Example 9

(2-Methyl-4-pyrrolidin-1-yl-quinolin-7-ylmethyl)-(3-trifluoromethyl-phenyl)-amine The title compound was produced in accordance with the general method of example 13b from 4-chloro-2-methylquinoline-7-carbaldehyde (example 13a), 3-trifluoromethylaniline, and pyrrolidine. White solid, ISP-MS: m/e=386.3 ([M+H]$^+$).

Example 10

2-Methyl-7-phenoxymethyl-4-pyrrolidin-1-yl-quinoline

The title compound was produced in accordance with the general method of example 20 from (4-chloro-2-methyl-quinolin-7-yl)-methanol (example 2c), phenol, and pyrrolidine. Light brown solid, ISP-MS: m/e=344.4 ([M+H]$^+$).

Example 11

4-Azepan-1-yl-2-methyl-7-(3-trifluoromethyl-phenoxymethyl)-quinoline

The title compound was produced in accordance with the general method of example 20 from (4-chloro-2-methyl-quinolin-7-yl)-methanol (example 2c), 3-trifluoromethylphenol, and azepane. Off-white solid, ISP-MS: m/e=415.3 ([M+H]$^+$).

Example 12

7-(3-Methoxy-phenoxymethyl)-2-methyl-4-pyrrolidin-1-yl-quinoline

The title compound was produced in accordance with the general method of example 20 from (4-chloro-2-methyl-quinolin-7-yl)-methanol (example 2c), 3-methoxyphenol, and pyrrolidine. Yellow solid, ISP-MS: m/e=349.4 ([M+H]$^+$).

Example 13

4-[(2-Methyl-4-pyrrolidin-1-yl-quinolin-7-ylmethyl)-amino]-benzonitrile a) 4-Chloro-2-methyl-quinoline-7-carbaldehyde Method A: A mixture of (4-chloro-2-methyl-quinolin-7-yl)-methanol (example 2c, 500 mg, 2.41 mmol) and manganese dioxide (2.09 g, 24.1 mmol) was refluxed in dichloromethane (14 mL) for 3.5 h. After cooling, insoluble material was removed by filtration through a dicalite pad, and the filtrate was evaporated to yield the title compound (403 mg, 81%). White solid, ISP-MS: m/e=206.1 ([M+H]$^+$).

Method B: Diisobutylaluminum hydride (1 M solution in dichloromethane, 0.60 mL, 0.60 mmol) was added dropwise to a solution of 4-chloro-2-methyl-quinoline-7-carbonitrile (example 2a, 100 mg, 0.49 mmol) in dichloromethane (2 mL) at −20° C. After 2 h the temperature was allowed to reach 0° C., then after 2 h, the reaction was stopped by addition of 1 M aq. sodium potassium tartrate solution The organic layer was separated, washed with brine, dried (MgSO$_4$), and evaporated. Chormatography (SiO$_2$, hexane/ethyl acetate 4:1, then dichloromethane/methanol 19:1) yielded the title compound (40 mg, 39%).

b) 4-[(2-Methyl-4-pyrrolidin-1-yl-quinolin-7-ylmethyl)-amino]-benzonitrile

Sodium borohydride (101 mg, 2.68 mmol) was added portionwise at 0° C. to a mixture of 4-chloro-2-methyl-quinoline-7-carbaldehyde (101 mg, 0.49 mmol), 3-trifluoromethylaniline (72 mg, 0.45 mmol), sodium sulfate (70 mg, 0.49 mmol) and sodium acetate (121 mg, 1.48 mmol) in ethanol (2 mL) and acetic acid (1 mL). The reaction mixture was stirred 2 h at 0° C. and 1 h at r.t., then poured onto 1 M aq. sodium hydroxide solution and extracted with ether. The organic layer was washed with brine, dried (MgSO$_4$) and evaporated. The material obtained (160 mg) was taken up in pyrrolidine (0.97 mL, 13.7 mmol) and heated for 16 h for at 80° C. After cooling the solution was partitioned between ethyl acetate and 1 M aq. carbonate buffer (pH 10.3). The organic layer was washed with brine, dried (MgSO$_4$), and evaporated. Chormatography (SiO$_2$, hexane/ethyl acetate 1:1, then dichloromethane/methanol 19:1) yielded a solid which was triturated in ether, filtered and dried to afford the title compound (58 mg, 33%). White solid, ISP-MS: m/e=343.3 ([M+H]$^+$).

Example 14

7-(2-Methoxy-phenoxymethyl)-2-methyl-4-pyrrolidin-1-yl-quinoline oxalate

Diisopropylazodicarboxylate (97 mg, 0.48 mmol) was added dropwise at r.t. to a solution of (4-chloro-2-methyl-quinolin-7-yl)-methanol (example 2c, 100 mg, 0.48 mmol), triphenylphosphine (126 mg, 0.48 mmol), 2-methoxyphenol (60 mg, 0.48 mmol) in dichloromethane (2.5 mL). After shaking 24 h at r.t., the solvent was evaporated, and the residue was taken up in pyrrolidine (1.37 g, 19.2 mmol) and shaken for 23 h at 80° C. After cooling the reaction mixture was partitioned between sat. aq. ammonium chloride solution and dichloromethane, the organic layer was washed with brine, dried (MgSO$_4$), and evaporated. Chromatography (SiO$_2$, dichloromethane/methanol 19:1) yielded a yellowish solid which was dissolved in ethanol and treated with 20% ethanolic oxalic acid solution. The precipitate was collected by filtration and dried to afford the title compound (90 mg, 43%). Off-white solid, ISP-MS: m/e=349.4 ([M+H—C$_2$H$_2$O$_4$]$^+$).

Example 15

7-(2-Fluoro-phenoxymethyl)-2-methyl-4-pyrrolidin-1-yl-quinoline

The title compound was produced in accordance with the general method of example 20 from (4-chloro-2-methyl-quinolin-7-yl)-methanol (example 2c), 2-fluorophenol, and pyrrolidine. Light brown solid, ISP-MS: m/e=337.3 ([M+H]$^+$).

Example 16

7-(3-Fluoro-phenoxymethyl)-2-methyl-4-pyrrolidin-1-yl-quinoline oxalate

The title compound was produced in accordance with the general method of example 14 from (4-chloro-2-methyl-quinolin-7-yl)-methanol (example 2c), 3-fluorophenol, and pyrrolidine. Off-white solid, ISP-MS: m/e=337.3 ([M+H—C$_2$H$_2$O$_4$]$^+$).

Example 17

2-Methyl-4-pyrrolidin-1-yl-7-o-tolyloxymethyl-quinoline oxalate

The title compound was produced in accordance with the general method of example 14 from (4-chloro-2-methyl-quinolin-7-yl)-methanol (example 2c), 2-methylphenol, and pyrrolidine. Off-white solid, ISP-MS: m/e=333.3 ([M+H—C$_2$H$_2$O$_4$]$^+$).

Example 18

2-Methyl-4-pyrrolidin-1-yl-7-m-tolyloxymethyl-quinoline oxalate

The title compound was produced in accordance with the general method of example 14 from (4-chloro-2-methyl-quinolin-7-yl)-methanol (example 2c), 3-methylphenol, and pyrrolidine. Off-white solid, ISP-MS: m/e=333.4 ([M+H—$C_2H_2O_4$]$^+$).

Example 19

2-Methyl-4-pyrrolidin-1-yl-7-p-tolyloxymethyl-quinoline oxalate

The title compound was produced in accordance with the general method of example 14 from (4-chloro-2-methyl-quinolin-7-yl)-methanol (example 2c), 4-methylphenol, and pyrrolidine. Off-white solid, ISP-MS: m/e=333.3 ([M+H—$C_2H_2O_4$]$^+$).

Example 20

7-(4-Fluoro-phenoxymethyl)-2-methyl-4-pyrrolidin-1-yl-quinoline

Diisopropylazodicarboxylate (97 mg, 0.48 mmol) was added dropwise at r.t. to a solution of (4-chloro-2-methyl-quinolin-7-yl)-methanol (example 2c, 100 mg, 0.48 mmol), triphenylphosphine (126 mg, 0.48 mmol), and 4-fluorophenol (54 mg, 0.54 mmol) in dichloromethane (2.5 mL). After shaking 24 h at r.t., the solvent was evaporated, and the residue was taken up in pyrrolidine (1.37 g, 19.2 mmol) and shaken for 23 h at 80° C. After cooling the reaction mixture was partitioned between sat. aq. ammonium chloride solution and dichloromethane, the organic layer was washed with brine, dried (MgSO$_4$), and evaporated. Chromatography (SiO$_2$, dichloromethane/methanol 19:1) yielded the title compound (66 mg, 41%). Off-white solid, ISP-MS: m/e=337. ([M+H]$^+$).

Example 21

[3-Methoxy-4-(2-methyl-4-pyrrolidin-1-yl-quinolin-7-ylmethoxy)-phenyl]-pyrrolidin-1-yl-methanone

The title compound was produced in accordance with the general method of example 20 from (4-chloro-2-methyl-quinolin-7-yl)-methanol (example 2c), 4-hydroxy-3-methoxybenzonitrile, and pyrrolidine. Light brown solid, ISP-MS: m/e=446.3 ([M+H]$^+$).

Example 22

2-Methyl-4-pyrrolidin-1-yl-quinoline-7-carboxylic acid amide a) 7-Iodo-2-methyl-4-pyrrolidin-1-yl-quinoline

A suspension of 4-chloro-7-iodo-2-methylquinoline (EP497371, 2.00 g, 6.59 mmol) in ethanol (20 mL) was treated sucessively with pyrrolidine (1.28 g, 18.0 mmol), pyridine (0.2 mL) and potassium iodide (50 mg, 0.30 mmol), and the resulting mixture was refluxed for 24 h. After concentration in vacuo, the residue was taken up in water (50 mL) and basified to pH 12 by addition of 2 M aq. sodium hydroxide solution. The precipitate was collected by filtration, washed with water (20 mL) and ether (20 mL) and dried to afford the title compound (1.95 g, 87%). Off-white solid, m.p. 99–102° C.

b) 2-Methyl-4-pyrrolidin-1-yl-quinoline-7-carbonitrile (72-3186)

A suspension of 7-iodo-2-methyl-4-pyrrolidin-1-yl-quinoline (1.50 g, 4.43 mmol), potassium cyanide (578 mg, 8.87 mmol), tetrakis(triphenylphosphine)palladium(0) (256 mg, 0.22 mmol), and copper iodide (85 mg, 0.44 mmol) in acetonitrile (10 mL) was refluxed for 90 min. After cooling the mixture was diluted with ethyl acetate, filtered, and the filtrate was washed with brine, dried (Na$_2$SO$_4$), and evaporated. Chromatography (SiO$_2$, dichloromethane/methanol 19:1) yielded the title compound (791 mg, 75%). Light brown solid, ISP-MS: m/e=238.3 ([M+H]$^+$).

c) 2-Methyl-4-pyrrolidin-1-yl-quinoline-7-carboxylic acid amide

A solution of 2-methyl-4-pyrrolidin-1-yl-quinoline-7-carbonitrile (100 mg, 0.42 mol) in dichloromethane (1 mL) was treated at 0° C. with 30% aq. hydrogen peroxide solution (0.5 mL), tetrabutylammonium hydrogen sulfate (29 mg, 84 µmol), and 20% aq. sodium hydroxide solution (0.5 mL). After removal of the ice bath, the two-phase mixture was stirred at r.t. for 2 h, then the organic layer was separated, washed with brine, dried (MgSO$_4$), and evaporated. Chromatography (SiO$_2$, dichloromethane/methanol 9:1) afforded the title compound (65 mg, 60%). Light brown solid, ISP-MS m/e=256.1 ([M+H]$^+$).

Example 23

4-Azepan-1-yl-7-methoxymethyl-2-methyl-quinoline

The title compound was produced in accordance with the general method of example 25 from (4-azepan-1-yl-2-methyl-quinolin-7-yl)-methanol (example 3) and iodomethane. Light yellow solid, ISP-MS: m/e=285.3 ([M+H]$^+$).

Example 24

2-Methyl-7-(pyridin-4-yloxymethyl)-4-pyrrolidin-1-yl-quinoline

Sodium hydride (55–65% dispersion in mineral oil, 40 mg, 1.0 mmol) was added to a mixture of (2-methyl-4-pyrrolidin-1-yl-quinolin-7-yl)-methanol (example 2, 100 mg, 0.41 mmol) and 4-chloropyridine hydrochloride (62 mg, 0.41 mmol), and the mixture was heated at 90° C. for 18 h. Then another portion of sodium hydride (40 mg) and 4-chloropyridine hydrochloride (62 mg) was added, and stirring at 90° C. was continued for 24 h. After cooling, the reaction mixture was partitioned between 1 M aq. sodium carbonate solution and ethyl acetate. The organic layer was separated, washed with brine, dried (MgSO$_4$), and evaporated. Chromatography (SiO$_2$, dichloromethane/methanol 9:1) afforded the title compound (32 mg, 24%). Yellow solid, ISP-MS: m/e=320.4 ([M+H]$^+$).

Example 25

4-Azepan-1-yl-7-(2-methoxy-ethoxymethyl)-2-methyl-quinoline

Sodium hydride (55–65% dispersion in mineral oil, 10 mg, 0.25 mmol) was added to a solution of (4-azepan-1-yl- 2-methyl-quinolin-7-yl)-methanol (example 3, 50 mg, 0.19 mmol) and 1-bromo-2-methoxy-ethane (15 mg, 0.19 mmol) in N,N-dimethylformamide (2 mL). After 22 h at 50° C., another portion of sodium hydride (10 mg) and 1-bromo-2-methoxyethane (15 mg) was added, and stirring was continued for 16 h. Then the reaction mixture was partitioned between 1 M aq. sodium carbonate solution and ethyl acetate. The organic layer was separated washed with brine, dried (MgSO$_4$), and evaporated. Chromatography (SiO$_2$, dichloromethane/methanol 9:1) yielded the title compound (20 mg, 33%). Yellow oil, ISP-MS: m/e=329.4 ([M+H]$^+$).

Example 26

7-(4-Methoxy-phenoxymethyl)-2-methyl-4-pyrrolidin-1-yl-quinoline

The title compound was produced in accordance with the general method of example 20 from (4-chloro-2-methyl-quinolin-7-yl)-methanol (example 2c), 4-methoxyphenol, and pyrrolidine. Off-white solid, ISP-MS: m/e=349.5 ([M+H]$^+$).

Example 27

(2-Methyl-4-pyrrolidin-1-yl-quinolin-7-yl)-pyrrolidin-1-yl-methanone (4-Chloro-2-methyl-quinolin-7-yl)-methanol (example 2, 200 mg, 0.80 mmol) was heated in pyrrolidine (2 mL) at 70° C. for 48 h. After cooling the reaction mixture was partitioned between sat. aq. ammonium chloride solution and dichloromethane. The organic layer was separated, dried (MgSO$_4$), and evaporated. Chromatography (SiO$_2$, CH$_2$Cl$_2$/MeOH 19:1) afforded the title compound (134 mg, 54%). Light yellow solid, ISP-MS: m/e=310.3 ([M+H]$^+$).

Example 28

2-Methyl-4-pyrrolidin-1-yl-quinoline-7-carboxylic acid (4-cyano-phenyl)-amide

A suspension of 2-methyl-4-pyrrolidin-1-yl-quinoline-7-carboxylic acid amide (50 mg, 0.20 mmol), 4-iodobenzonitrile (45 mg, 0.20 mmol), xantphos (6.8 mg, 12 µmol), cesium carbonate (89 mg, 0.27 mmol), and palladium(II) acetate (1.8 mg, 8 µmol) in 1,4-dioxane (0.5 mL) was stirred under argon at 50° C. for 22 h, then the reaction mixture was partitioned between sat. aq. sodium hydrogencarbonate solution and dichloromethane. The organic layer was separated, washed with brine, dried (MgSO$_4$), and evaporated. Chromatography (SiO$_2$, dichloromethane/methanol 19:1) afforded the title compound (18 mg, 26%). Light yellow solid, ISP-MS: m/e=357.3 ([M+H]$^+$).

Example 29

2-Methyl-4-pyrrolidin-1-yl-7-pyrrolidin-1-ylmethyl-quinoline

Lithium aluminumhydride (20 mg, 0.52 mmol) was added to a solution of (2-methyl-4-pyrrolidin-1-yl-quinolin-7-yl)-pyrrolidin-1-yl-methanone (example 27, 80 mg, 0.26 mmol) in tetrahydrofuran (1 mL), and the reaction mixture was stirred at room temperature for 3 h, then 1 M aq. potassium sodium tartrate solution (10 mL) and ethyl acetate (10 mL) were added. After 15 min, the organic layer was separated, washed with brine, dried (MgSO$_4$), and evaporated. Chromatography (SiO$_2$, dichloromethane/methanol 9:1) afforded the title compound (31 mg, 41%). Off-white solid, ISP-MS: m/e=337.3 ([M+H]$^+$).

Example 30

2-Methyl-4-pyrrolidin-1-yl-quinoline-7-carboxylic acid butylamide (4-Chloro-2-methyl-quinolin-7-yl)-methanol (example 2, 200 mg, 0.80 mmol) was refluxed in butylamine (2 mL) for 6 h. After cooling the reaction mixture was partitioned between sat. aq. ammonium chloride solution and dichloromethane. The organic layer was separated, dried (MgSO$_4$), and evaporated. The residue was chromatographed (SiO$_2$, CH$_2$Cl$_2$/MeOH 19:1) to produce a yellow oil, which was heated in pyrrolidine (2 mL) at 70° C. for 16 h. After cooling the reaction mixture was partitioned between sat. aq. ammonium chloride solution and dichloromethane. The organic layer was separated, dried (MgSO$_4$), and evaporated. Chromatography (SiO$_2$, dichloromethane/methanol 19:1) afforded the title compound (108 mg, 43%). White solid, ISP-MS: m/e=312.3 ([M+H]$^+$).

Example 31

2-(2-Methyl-4-pyrrolidin-1-yl-quinolin-7-yl-methoxy)-benzonitrile

The title compound was produced in accordance with the general method of example 6 from (2-methyl-4-pyrrolidin-1-yl-quinolin-7-yl)-methanol (example 2) and 2-fluorobenzonitrile. White solid, ISP-MS: m/e=344.4 ([M+H]$^+$).

Example 32

2-Chloro-4-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2-chloro-4-fluorobenzonitrile. Light yellow solid, ISP-MS: m/e=378.3 ([M+H]$^+$).

Example 33

4-(2-Methyl-4-pyrrolidin-1-yl-quinolin-7-yl-methoxy)-2-trifluoromethyl-benzonitrile The title compound was produced in accordance with the general method of example 6 from (2-methyl-4-pyrrolidin-1-yl-quinolin-7-yl)-methanol (example 2) and 4-fluoro-2-trifluoromethylbenzonitrile. White solid, ISP-MS: m/e=412.3 ([M+H]$^+$).

Example 34

Butyl-(2-methyl-4-pyrrolidin-1-yl-quinolin-7-ylmethyl)-amine

The title compound was produced in accordance with the general method of example 29 from 2-methyl-4-pyrrolidin-1-yl-quinoline-7-carboxylic acid butylamide (example 30). Yellow oil, ISP-MS: m/e=298.4 ([M+H]$^+$).

Example 35

Mixture (1:1) of 2-fluoro-4-(2-methyl-4-pyrrolidin-1-yl-quinolin-7-ylmethoxy)-benzonitrile and 4-fluoro-2-(2-methyl-4-pyrrolidin-1-yl-quinolin-7-ylmethoxy)-benzonitrile The title compounds were produced in accordance with the general method of example 6 from (2-methyl-4-pyrrolidin-1-yl-quinolin-7-yl)-methanol (example 2) and 2,4-difluorobenzonitrile. Yellow solid, ISP-MS: m/e=362.2 ([M+H]$^+$). The obtained compounds can be separated by conventional methods such as for example chromatography.

Example 36

3-Fluoro-4-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 3,4-difluorobenzonitrile. Light yellow solid, ISP-MS: m/e=362.3 ([M+H]$^+$).

Example 37

3-Chloro-4-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 3-chloro-4-fluorobenzonitrile. Light yellow solid, ISP-MS: m/e=378.3 ([M+H]$^+$).

Example 38

4-(2-Methyl-4-pyrrolidin-1-yl-quinolin-7-ylmethoxy)-phthalonitrile

The title compound was produced in accordance with the general method of example 6 from (2-methyl-4-pyrrolidin-1-yl-quinolin-7-yl)-methanol (example 2) and 4-fluorophthalonitrile. Light yellow solid, ISP-MS: m/e=369.3 ([M+H]$^+$).

Example 39

5-Bromo-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 5-bromo-2-fluorobenzonitrile. Light yellow solid, ISP-MS: m/e=422.3, 424.3 ([M+H]$^+$).

Example 40

4-(2-Methyl-4-pyrrolidin-1-yl-quinolin-7-ylmethoxy)-2-nitro-benzonitrile

The title compound was produced in accordance with the general method of example 6 from (2-methyl-4-pyrrolidin-1-yl-quinolin-7-yl)-methanol (example 2) and 4-fluoro-2-nitrobenzonitrile. Yellow solid, ISP-MS: m/e=389.3 ([M+H]$^+$).

Example 41

5-Fluoro-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2,5-difluorobenzonitrile. Light yellow solid, ISP-MS: m/e=362.3 ([M+H]$^+$).

Example 42

2-Chloro-6-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2-chloro-6-fluorobenzonitrile. Light yellow solid, ISP-MS: m/e=378.4 ([M+H]$^+$).

Example 43

3-Fluoro-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2,3-difluorobenzonitrile. Light yellow solid, ISP-MS: m/e=362.3 ([M+H]$^+$).

Example 44

2-Iodo-6-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2-fluoro-6-iodobenzonitrile. Light yellow solid, ISP-MS: m/e=470.2 ([M+H]$^+$).

Example 45

4-(2-Methyl-4-pyrrolidin-1-yl-quinolin-7-ylmethoxy)-3-trifluoromethyl-benzonitrile The title compound was produced in accordance with the general method of example 6 from (2-methyl-4-pyrrolidin-1-yl-quinolin-7-yl)-methanol (example 2) and 4-fluoro-3-trifluoromethylbenzonitrile. Light yellow solid, ISP-MS: m/e=412.4 ([M+H]$^+$).

Example 46

2-(2-Methyl-4-pyrrolidin-1-yl-quinolin-7-ylmethoxy)-6-trifluoromethyl-benzonitrile The title compound was produced in accordance with the general method of example 6 from (2-methyl-4-pyrrolidin-1-yl-quinolin-7-yl)-methanol (example 2) and 2-fluoro-6-trifluoromethylbenzonitrile. Light yellow solid, ISP-MS: m/e=412.4 ([M+H]$^+$).

Example 47

2-(2-Methyl-4-pyrrolidin-1-yl-quinolin-7-yl-methoxy)-5-trifluoromethyl-benzonitrile

The title compound was produced in accordance with the general method of example 6 from (2-methyl-4-pyrrolidin-1-yl-quinolin-7-yl)-methanol (example 2) and 2-fluoro-5-trifluoromethylbenzonitrile. Light yellow solid, ISP-MS: m/e=412.4 ([M+H]$^+$).

Example 48

3,5-Difluoro-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2,3,5-trifluoromethylbenzonitrile. Light yellow solid, ISP-MS: m/e=380.4 ([M+H]$^+$).

Example 49

5-Methyl-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 2-fluoro-5-methylbenzonitrile. Light yellow solid, ISP-MS: m/e=358.4 ([M+H]$^+$).

Example 50

4-Bromo-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 4-bromo-2-fluorobenzonitrile. Light yellow solid, ISP-MS: m/e=422.4, 424.4 ([M+H]$^+$).

Example 51

4-Chloro-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 4-chloro-2-fluorobenzonitrile. Light yellow solid, ISP-MS: m/e=378.4 ([M+H]$^+$).

Example 52

3-Fluoro-2-(2-methyl-4-pyrrolidin-1-yl-quinolin-7-ylmethoxy)-4-trifluoromethyl-benzonitrile

The title compound was produced in accordance with the general method of example 6 from (2-methyl-4-pyrrolidin-1-yl-quinolin-7-yl)-methanol (example 2) and 2,3-difluoro-4-trifluoromethylbenzonitrile. Light yellow solid, ISP-MS: m/e=430.6 ([M+H]$^+$).

Example 53

5-Chloro-2-(2-methyl-4-pyrrolidin-1-yl-quinolin-7-ylmethoxy)-benzonitrile

The title compound was produced in accordance with the general method of example 6 from (2-methyl-4-pyrrolidin-1-yl-quinolin-7-yl)-methanol (example 2) and 5-chloro-2-fluorobenzonitrile. Light yellow solid, ISP-MS: m/e=378.4 ([M+H]$^+$).

Example 54

4-[2-Methyl-4-(4-methyl-piperazin-1-yl)-quinolin-7-ylmethoxy]-benzonitrile a) 4-(4-Chloro-2-methyl-quinolin-7-ylmethoxy)-benzonitrile

Sodium hydride (55–65% dispersion in mineral oil, 220 mg, 5.50 mmol) was added to a solution of (4-chloro-2-methyl-quinolin-7-yl)-methanol (example 2c, 1.10 g, 5.30 mmol) and 4-fluorobenzonitrile (642 mg, 5.30 mmol) in N,N-dimethylformamide (20 mL), and the resulting mixture was stirred at 50° C. for 3 h. After cooling the mixture was partitioned between sat. aq. ammonium chloride solution and dichloromethane, the organic layer was separated, washed with brine, dried (MgSO$_4$), and evaporated. Chromatography (SiO$_2$, dichloromethane/methanol 19:1) yielded the title compound (1.28 g, 78%). Yellow solid, ISP-MS: m/e=309.3 ([M+H]$^+$).

b) 4-[2-Methyl-4-(4-methyl-piperazin-1-yl)-quinolin-7-ylmethoxy]-benzonitrile

A solution of 4-(4-chloro-2-methyl-quinolin-7-ylmethoxy)-benzonitrile (100 mg, 0.32 mmol) and 1-methylpiperazine (81 mg, 0.81 mmol) in 1-methylpyrrolidin-2-one (1.5 mL) was stirred at 100° C. for 24 h. After cooling the reaciton mixture was partitioned between sat. aq. sodium hydrogencarbonate solution and dichloromethane, the organic layer was separated, washed with brine, dried (MgSO$_4$), and evaporated. Chromatography (SiO$_2$, dichloromethane/methanol 19:1) yielded the title compound (80 mg, 66%). Light yellow oil, ISP-MS: m/e=373.5 ([M+H]$^+$).

Example 55

2-(2-Methyl-4-pyrrolidin-1-yl-quinolin-7-yl-methoxy)-4-trifluoromethyl-benzonitrile

The title compound was produced in accordance with the general method of example 6 from (2-methyl-4-pyrrolidin-1-yl-quinolin-7-yl)-methanol (example 2) and 2-fluoro-4-trifluoromethylbenzonitrile. White solid, ISP-MS: m/e=412.4 ([M+H]$^+$).

Example 56

4-(2-Methyl-4-piperidin-1-yl-quinolin-7-ylmethoxy)-benzonitrile

A solution of 4-(4-chloro-2-methyl-quinolin-7-ylmethoxy)-benzonitrile (example 54a, 100 mg, 0.32 mmol) in piperidine (1 mL) was heated at 100° C. for 21 h. After cooling the reaciton mixture was partitioned between sat. aq. sodium hydrogencarbonate solution and dichloromethane, the organic layer was separated, washed with brine, dried (MgSO$_4$), and evaporated. Chromatography (SiO$_2$, dichlo-

Example 57

(S)-4-[4-(3-Dimethylamino-pyrrolidin-1-yl)-2-methyl-quinolin-7-ylmethoxy]-benzonitrile The title compound was produced in accordance with the general method of example 54b from 4-(4-chloro-2-methyl-quinolin-7-ylmethoxy)-benzonitrile (example 54a) and (S)-3-(dimethylamino)-pyrrolidine. Brown solid, ISP-MS: m/e=387.4 ([M+H]$^+$).

Example 58

4-[2-Methyl-4-(4-methyl-[1,4]diazepan-1-yl)-quinolin-7-ylmethoxy]-benzonitrile

The title compound was produced in accordance with the general method of example 54b from 4-(4-chloro-2-methyl-quinolin-7-ylmethoxy)-benzonitrile (example 54a) and 1-methylhomopiperazine. Yellow solid, ISP-MS: m/e=387.4 ([M+H]$^+$).

Example 59

(2,6-Dimethyl-4-pyrrolidin-1-yl-quinolin-7-yl)-methanol a) 4-Chloro-7-iodo-2,6-dimethyl-quinoline A suspension of 3-iodo-4-methylaniline (50.0 g, 215 mmol) and toluene-4-sulfonic acid monohydrate (430 mg, 2.15 mmol) was refluxed for 2 h in cyclohexane (100 mL), allowing the water formed to collect in a Dean-Stark trap, then after cooling insoluble material was removed by filtration and the filtrate evaporated. The residue was dissolved in Dowtherm® A (25 mL) and added dropwise to hot (ca. 250° C.) Dowtherm® A. After 15 min the reaction mixture was allowed to reach room temperature, then heptane (150 mL) was added and the precipitate collected by filtration. This material was triturated in ethyl acetate to afford a 1:1 mixture of 7-iodo-2,6-methyl-1H-quinolin-4-one and 5-iodo-2,6-dimethyl-1H-quinolin-4-one (46.4 g). Chlorination of these isomeric quinolones was accomplished in accordance with the general method of example 88d. Recrystallization of the product mixture thus produced (4-chloro-7-iodo-2,6-dimethyl-quinoline and 4-chloro-5-iodo-2,6-dimethyl-quinoline) in hexane/ethyl acetate 9:1 (150 mL) afforded the title compound (7.55 g, 11%). Light brown solid, ISP-MS: m/e=318.1 ([M+H]$^+$).

b) 4-Chloro-2,6-dimethyl-quinoline-7-carboxylic acid ethyl ester

The title compound was produced in accordance with the general method of example 2b (method B) from 4-chloro-7-iodo-2,6-dimethyl-quinoline. White solid, ISP-MS: m/e=264.3 ([M+H]$^+$).

c) (4-Chloro-2,6-dimethyl-quinolin-7-yl)-methanol

The title compound was produced in accordance with the general method of example 2c from 4-chloro-2,6-dimethyl-quinoline-7-carboxylic acid ethyl ester. White solid, ISP-MS: m/e=222.2 ([M+H]$^+$).

d) (2,6-Dimethyl-4-pyrrolidin-1-yl-quinolin-7-yl)-methanol

The title compound was produced in accordance with the general method of example 2d from (4-chloro-2,6-dimethyl-quinolin-7-yl)-methanol and pyrrolidine. White solid, ISP-MS: m/e=257.2 ([M+H]$^+$).

Example 60

4-(2,6-Dimethyl-4-pyrrolidin-1-yl-quinolin-7-ylmethoxy)-benzonitrile

The title compound was produced in accordance with the general method of example 6 from (2,6-dimethyl-4-pyrrolidin-1-yl-quinolin-7-yl)-methanol (example 59) and 4-fluorobenzonitrile. White solid, ISP-MS: m/e=358.3 ([M+H]$^+$).

Example 61

2-(2,6-Dimethyl-4-pyrrolidin-1-yl-quinolin-7-ylmethoxy)-benzonitrile

The title compound was produced in accordance with the general method of example 6 from (2,6-dimethyl-4-pyrrolidin-1-yl-quinolin-7-yl)-methanol (example 59) and 2-fluorobenzonitrile. Yellow foam, ISP-MS: m/e=358.3 ([M+H]$^+$).

Example 62

{2-Methyl-4-[(S)-2-(tetrahydro-pyran-2-yloxymethyl)-pyrrolidin-1-yl]-quinolin-7-yl}-methanol a) (S)-2-(Tetrahydro-pyran-2-yloxymethyl)-pyrrolidine-1-carboxylic acid benzyl ester A solution of L-prolinol (1.00 g, 4.94 mmol) in N,N-dimethylformamide (5 mL) was cooled to 0° C. and treated with sodium hydrogencarbonate (831 mg, 9.87 mmol) and benzyl chloroformate (843 mg, 4.94 mmol). After removal of the ice bath the reaction mixture was stirred 1 h at r.t. then poured onto ice and extracted with ethyl acetate. The organic layer was washed with brine, dried (MgSO$_4$) and evaporated. The residue was taken up in dichloromethane (5 mL), treated with 3,4-dihydro-2H-pyran (1.25 g, 14.8 mmol) and pyridinium toluene-4-sulfonate (1.37 g, 5.43 mmol) and stirred for 48 h at r.t., then evaporated. The residue was partitioned between ethyl acetate and water, the organic layer was washed with brine, dried (MgSO$_4$), and evaporated. Chromatography (SiO2, hexane/ethyl acetate 3:1) yielded the title compound (451 mg, 29%). Colourless liquid, ISP-MS: m/e=320.4 ([M+H]$^+$).

b) (S)-2-(Tetrahydro-pyran-2-yloxymethyl)-pyrrolidine (S)-2-(Tetrahydro-pyran-2-yloxymethyl)-pyrrolidine-1-carboxylic acid benzyl ester (445 mg, 1.39 mmol) was dissolved in ethanol (9 mL) and hydrogenated at atmospheric pressure and room temperature in the presence of 10% paladium on charcoal (10 mg). After 16 h the reaction mixture was passed through a filter aid and evaporated to afford the title compound which was used without further purification (255 mg, 99%). Black liquid, ISP-MS: m/e=186.3 ([M+H]$^+$).

c) {2-Methyl-4-[(S)-2-(tetrahydro-pyran-2-yloxymethyl)-pyrrolidin-1-yl]-quinolin-7-yl}-methanol The title compound was produced in accordance with the general method of example 54b from (4-chloro-2-methyl-quinolin-7-yl)-methanol (example 2c) and (S)-2-(tetrahydro-pyran-2-yloxymethyl)-pyrrolidine. Orange gum, ISP-MS: m/e=357.3 ([M+H]$^+$).

(The previous example continues:) romethane/methanol 19:1) yielded the title compound (40 mg, 32%). Light yellow gum, ISP-MS: m/e=358.4 ([M+H]$^+$).

Example 63

4-[(2-Methyl-4-pyrrolidin-1-yl-quinolin-7-ylmethyl)-amino]-2-trifluoromethyl-benzonitrile a) 4-[(4-Chloro-2-methyl-quinolin-7-ylmethyl)-amino]-2-trifluoromethyl-benzonitrile To a solution of 4-chloro-2-methyl-quinoline-7-carbaldehyde (example 13a, 180 mg, 0.875 mmol) in ethanol (3 mL) were added 4-amino-2-trifluoromethyl-benzonitrile (163 mg, 0.875 mmol), 25% aq. hydrochloric acid solution (1.5 mL), and sodium borohydride (207 mg, 5.25 mmol). The reaction mixture was stirred 16 h at r.t., then partitioned between ethyl acetate and 1 M aq. sodium hydroxide solution. The organic layer was washed with brine, dried (MgSO$_4$), and evaporated. Flash chromatography (SiO$_2$, hexane/ethyl acetate 1:1 afforded the title compound (123 mg, 37%). Off-white solid, ISP-MS: m/e=376.3 ([M+H]$^+$).

b) 4-[(2-Methyl-4-pyrrolidin-1-yl-quinolin-7-ylmethyl)-amino]-2-trifluoromethyl-benzonitrile The title compound was produced in accordance with the general method of example 56 from 4-[(4-chloro-2-methyl-quinolin-7-ylmethyl)-amino]-2-trifluoromethyl-benzonitrile and pyrrolidine. White foam, ISP-MS: m/e=411.3 ([M+H]$^+$).

Example 64

(S)-[1-(7-Hydroxymethyl-2-methyl-quinolin-4-yl)-pyrrolidin-2-yl]-methanol

A solution of {2-methyl-4-[(S)-2-(tetrahydro-pyran-2-yloxymethyl)-pyrrolidin-1-yl]-quinolin-7-yl}-methanol (50 mg, 0.14 mmol) and pyridinium toluene-4-sulfonate (39 mg, 0.15 mmol) in ethanol (1 mL) was stirred at 55° C. for 72 h, then partitioned between ethyl acetate and 1 M aq. sodium hydroxide solution. The organic layer was washed with brine, dried (MgSO$_4$), and evaporated. Flash chromatography (SiO$_2$, CH$_2$Cl$_2$/MeOH/NH$_4$OH 90:10:0.1) gave the title compound (25 mg, 65%). Yellow gum, ISP-MS: m/e=273.3 ([M+H]$^+$).

Example 65

(S)-4-[4-(2-Hydroxymethyl-pyrrolidin-1-yl)-2-methyl-quinolin-7-ylmethoxy]-benzonitrile The title compound was produced in accordance with the general method of example 54b from 4-(4-chloro-2-methyl-quinolin-7-ylmethoxy)-benzonitrile (example 54a) and L-prolinol. Light yellow foam, ISP-MS: m/e=374.5 ([M+H]$^+$).

Example 66

(S)-4-[4-(2-Hydroxymethyl-pyrrolidin-1-yl)-2-methyl-quinolin-7-ylmethoxy]-2-trifluoromethyl-benzonitrile a) 4-(4-Chloro-2-methyl-quinolin-7-ylmethoxy)-2-trifluoromethyl-benzonitrile The title compound was produced in accordance with the general method of example 54a from (4-chloro-2-methyl-quinolin-7-yl)-methanol (example 2c) and 4-fluoro-2-trifluoromethylbenzonitrile. Off-white solid, ISP-MS: m/e=377.3 ([M+H]$^+$).

b) (S)-4-[4-(2-Hydroxymethyl-pyrrolidin-1-yl)-2-methyl-quinolin-7-ylmethoxy]-2-trifluoromethyl-benzonitrile The title compound was produced in accordance with the general method of example 54b from 4-(4-chloro-2-methyl-quinolin-7-ylmethoxy)-2-trifluoromethyl-benzonitrile and L-prolinol. Light yellow solid, ISP-MS: m/e=442.4 ([M+H]$^+$).

Example 67

(S)-4-[4-(2-Hydroxymethyl-pyrrolidin-1-yl)-2-methyl-quinolin-7-ylmethoxy]-3-trifluoromethyl-benzonitrile a) 4-(4-Chloro-2-methyl-quinolin-7-ylmethoxy)-3-trifluoromethyl-benzonitrile The title compound was produced in accordance with the general method of example 54a from (4-chloro-2-methyl-quinolin-7-yl)-methanol (example 2c) and 4-fluoro-3-trifluoromethylbenzonitrile. Off-white solid, ISP-MS: m/e=377.3 ([M+H]$^+$).

b) (S)-4-[4-(2-Hydroxymethyl-pyrrolidin-1-yl)-2-methyl-quinolin-7-ylmethoxy]-3-trifluoromethyl-benzonitrile The title compound was produced in accordance with the general method of example 54b from 4-(4-chloro-2-methyl-quinolin-7-ylmethoxy)-3-trifluoromethyl-benzonitrile and L-prolinol. Light yellow solid, ISP-MS: m/e=442.4 ([M+H]$^+$).

Example 68

(S)-4-[4-(2-Hydroxymethyl-pyrrolidin-1-yl)-2-methyl-quinolin-7-ylmethoxy]-phthalonitrile a) 4-(4-Chloro-2-methyl-quinolin-7-ylmethoxy)-phthalonitrile The title compound was produced in accordance with the general method of example 54a from (4-chloro-2-methyl-quinolin-7-yl)-methanol (example 2c) and 4-fluorophthalonitrile. White foam, ISP-MS: m/e=334.2 ([M+H]$^+$).

b) (S)-4-[4-(2-Hydroxymethyl-pyrrolidin-1-yl)-2-methyl-quinolin-7-ylmethoxy]-phthalonitrile The title compound was produced in accordance with the general method of example 54b from 4-(4-chloro-2-methyl-quinolin-7-ylmethoxy)-phthalonitrile and L-prolinol. White solid, ISP-MS: m/e=399.5 ([M+H]$^+$).

Example 69

(S)-2-[4-(2-Hydroxymethyl-pyrrolidin-1-yl)-2-methyl-quinolin-7-ylmethoxy]-benzonitrile a) 2-(4-Chloro-2-methyl-quinolin-7-ylmethoxy)-benzonitrile The title compound was produced in accordance with the general method of example 54a from (4-chloro-2-methyl-quinolin-7-yl)-methanol (example 2c) and 2-fluorobenzonitrile. Light yellow solid, ISP-MS: m/e=309.2 ([M+H]$^+$).

b) (S)-2-[4-(2-Hydroxymethyl-pyrrolidin-1-yl)-2-methyl-quinolin-7-ylmethoxy]-benzonitrile The title compound was produced in accordance with the general method of example 54b from 2-(4-chloro-2-methyl-quinolin-7-ylmethoxy)-benzonitrile and L-prolinol. Light yellow solid, ISP-MS: m/e=374.4 ([M+H]$^+$).

Example 70

4-(2,6-Dimethyl-4-pyrrolidin-1-yl-quinolin-7-yl-methoxy)-2-trifluoromethyl-benzonitrile The title compound was produced in accordance with the general method of example 6 from (2,6-dimethyl-4-pyrrolidin-1-yl-quinolin-7-yl)-methanol (example 59) and 4-fluoro-2-trifluoromethylbenzonitrile. White solid, ISP-MS: m/e=426.4 ([M+H]$^+$).

Example 71

4-(2,6-Dimethyl-4-pyrrolidin-1-yl-quinolin-7-yl-methoxy)-3-trifluoromethyl-benzonitrile The title compound was produced in accordance with the general method of example 6 from (2,6-dimethyl-4-pyrrolidin-1-yl-quinolin-7-yl)-methanol (example 59c) and 4-fluoro-3-trifluoromethylbenzonitrile. Light yellow solid, ISP-MS: m/e=426.4 ([M+H]$^+$).

Example 72

(S)-[4-(2-Methoxymethyl-pyrrolidin-1-yl)-2,6-dimethyl-quinolin-7-yl]-methanol

The title compound was produced in accordance with the general method of example 54b from (4-chloro-2,6-dimethyl-quinolin-7-yl)-methanol (example 59c) and (S)-2-(methoxymethyl)pyrrolidine. White foam, ISP-MS: m/e=301.4 ([M+H]$^+$).

Example 73

(R)-[4-(2-Methoxymethyl-pyrrolidin-1-yl)-2,6-dimethyl-quinolin-7-yl]-methanol

The title compound was produced in accordance with the general method of example 54b from (4-chloro-2,6-dimethyl-quinolin-7-yl)-methanol (example 59c) and (R)-2-(methoxymethyl)pyrrolidine. White foam, ISP-MS: m/e=301.3 ([M+H]$^+$).

Example 74

(S)-4-[4-(2-Methoxymethyl-pyrrolidin-1-yl)-2,6-dimethyl-quinolin-7-ylmethoxy]-benzonitrile hydrochloride The title compound was produced in accordance with the general method of example 6 from (S)-[4-(2-methoxymethyl-pyrrolidin-1-yl)-2,6-dimethyl-quinolin-7-yl]-methanol (example 72) and 4-fluorobenzonitrile and isolated as the hydrochloride salt. White solid, ISP-MS: m/e=402.5 ([M–Cl]$^+$).

Example 75

(R)-4-[4-(2-Methoxymethyl-pyrrolidin-1-yl)-2,6-dimethyl-quinolin-7-ylmethoxy]-benzonitrile; hydrochloride The title compound was produced in accordance with the general method of example 6 from (R)-[4-(2-methoxymethyl-pyrrolidin-1-yl)-2,6-dimethyl-quinolin-7-yl]-methanol (example 73) and 4-fluorobenzonitrile and isolated as the hydrochloride salt. White solid, ISP-MS: m/e=402.5 ([M–Cl]$^+$).

Example 76

(S)-[4-(3-Ethoxy-pyrrolidin-1-yl)-2,6-dimethyl-quinolin-7-yl]-methanol; hydrochloride The title compound was produced in accordance with the general method of example 54b from (4-chloro-2,6-dimethyl-quinolin-7-yl)-methanol (example 59c) and (S)-3-ethoxypyrrolidine (EP496274), and isolated as the hydrochloride salt. White foam, ISP-MS: m/e=301.4 ([M–Cl]$^+$).

Example 77

(S)-4-[4-(3-Ethoxy-pyrrolidin-1-yl)-2,6-dimethyl-quinolin-7-ylmethoxy]-benzonitrile; hydrochloride The title compound was produced in accordance with the general method of example 6 from (S)-[4-(3-Ethoxy-pyrrolidin-1-yl)-2,6-dimethyl-quinolin-7-yl]-methanol; hydrochloride (example 76) and 4-fluorobenzonitrile and isolated as the hydrochloride salt. White solid, ISP-MS: m/e=402.5 ([M–Cl]$^+$).

Example 78

(4-Azepan-1-yl-2,6-dimethyl-quinolin-7-yl)-methanol

The title compound was produced in accordance with the general method of example 3 from (4-chloro-2,6-dimethyl-quinolin-7-yl)-methanol (example 59c) and azepane. Light brown foam, ISP-MS: m/e=285.3 ([M+H]$^+$).

Example 79

4-[(2,6-Dimethyl-4-pyrrolidin-1-yl-quinolin-7-ylmethyl)-amino]-2-trifluoromethyl-benzonitrile formate a) 2,6-Dimethyl-4-pyrrolidin-1-yl-quinoline-7-carbaldehyde A mixture of (2,6-dimethyl-4-pyrrolidin-1-yl-quinolin-7-yl)-methanol (example 59, 140 mg, 0.585 mmol) and manganese dioxide (509 mg, 5.85 mmol) was stirred in dichloromethane (3 mL) at r.t. for 16 h, then insoluble material was removed by filtration through a dicalite pad, and the filtrate was evaporated to yield the title compound (122 mg, 82%). Yellow solid, ISP-MS: m/e=255.2 ([M+H]$^+$).

b) 4-[(2,6-Dimethyl-4-pyrrolidin-1-yl-quinolin-7-ylmethyl)-amino]-2-trifluoromethyl-benzonitrile formate The title compound was produced in accordance with the general method of example 63a from 2,6-dimethyl-4-pyrrolidin-1-yl-quinoline-7-carbaldehyde and 4-amino-2-trifluoromethylbenzonitrile, and isolated as the formate salt. White solid, ISP-MS: m/e=425.4 ([M–HCOO]$^+$).

Example 80

(S)-1-(7-Hydroxymethyl-2,6-dimethyl-quinolin-4-yl)-pyrrolidin-3-ol

The title compound was produced in accordance with the general method of example 54b from (4-chloro-2,6-dimethyl-quinolin-7-yl)-methanol (example 59c) and (S)-3-pyrrolidinol. White solid, ISP-MS: m/e=273.3 ([M+H]+).

Example 81

(2-Chloro-6-methyl-4-pyrrolidin-1-yl-quinolin-7-yl)-methanol a) N,N'-Bis-(3-iodo-4-methyl-phenyl)-malonamide A mixture of diethyl malonate (16.0 g, 100 mmol) and 3-iodo-4-methylaniline (46.6 g, 200 mmol) was heated at 210° C. for 20 min, allowing the liberated ethanol to evaporate. After cooling the solid formed was triturated in hot ethanol (200 mL) to afford the title compound (43.4 g, 81%). Light brown solid, ISP-MS: m/e=535.0 ([M+H]+).

b) 4-Hydroxy-7-iodo-6-methyl-1H-quinolin-2-one

N,N'-Bis-(3-iodo-4-methyl-phenyl)-malonamide (43.4 g, 81.3 mmol) was added portionwise to a melt of aluminum chloride (32.5 g, 244 mmol) and sodium chloride (9.50 g, 163 mmol) at 150° C., then the mixture was heated at 250° C. for 20 min. After cooling the solid formed was suspended in hot water and collected by filtration. This crude material was suspended in hot 0.5 M aq. sodium hydroxide solution, insoluble material was removed by filtration, and the filtrate was acidified with 25% aq. hydrochloric acid solution. The precipitate was collected by filtration, washed with water and ethyl acetate, and dried to afford the title compound (6.85 g, 28%). Light brown solid, EI-MS: m/e=301.2 (M+).

c) 2,4-Dichloro-7-iodo-6-methyl-quinoline

A mixture of 4-hydroxy-7-iodo-6-methyl-1H-quinolin-2-one (2.00 g, 6.64 mmol) and phosphorus oxide chloride (20 mL) was refluxed for 2 h, then poured onto ice, and neutralized to pH 7. The precipitate was collected by filtration and dried. The crude product was suspended in ethyl acetate, insoluble material was separated by filtration, and the filtrate was evaporated to afford the title compound (1.80 g, 80%). Orange solid, EI-MS: m/e=336.9 (M+).

d) 2,4-Dichloro-6-methyl-quinoline-7-carboxylic acid ethyl ester

The title compound was produced in accordance with the general method of example 2b (method B) from 2,4-dichloro-7-iodo-6-methyl-quinoline. White solid, ISP-MS: m/e=284.1 ([M+H]+).

e) (2-Chloro-6-methyl-4-pyrrolidin-1-yl-quinolin-7-yl)-methanol

The title compound was produced in accordance with the general method of example 82 from 2,4-dichloro-6-methyl-quinoline-7-carboxylic acid ethyl ester and pyrrolidine. White solid, ISP-MS: m/e=277.3 ([M+H]+).

Example 82

(4-Azepan-1-yl-2-chloro-6-methyl-quinolin-7-yl)-methanol

Diisobutylaluminum hydride (1 M in tetrahydrofuran, 4.9 mL, 4.9 mmol) was added dropwise to a solution of 2,4-dichloro-6-methyl-quinoline-7-carboxylic acid ethyl ester (example 81c, 200 mg, 0.704 mmol) in tetrahydrofuran (10 mL), then after 20 min the reaction was stopped by addition of 2.5 M aq. magnesium sulfate solution (2 mL). The precipitate that formed after a few seconds was removed by filtration, and the filtrate was washed with brine, dried (MgSO4), and evaporated. The residue ((2,4-dichloro-6-methyl-quinolin-7-yl)-methanol) was dissolved in 1-methylpyrrolidin-2-one (3 mL), then azepane (349 mg, 3.52 mmol) and lithium chloride (119 mg, 2.82 mmol) were added, and the solution was heated at 80° C. for 16 h. After cooling ethyl acetate was added and the solution was washed with sat. aq. ammonium chloride solution and brine, dried (MgSO4), and evaporated. Flash chromatography (SiO2, hexane/ethyl acetate gradient) yielded the title compound (142 mg, 66%). Off-white solid, ISP-MS: m/e=305.3 ([M+H]+).

Example 83

(S)-4-[4-(3-Hydroxy-pyrrolidin-1-yl)-2,6-dimethyl-quinolin-7-ylmethoxy]-benzonitrile hydrochloride a) 4-(4-Chloro-2,6-dimethyl-quinolin-7-ylmethoxy)-benzonitrile The title compound was produced in accordance with the general method of example 54a from (4-chloro-2,6-dimethyl-quinolin-7-yl)-methanol (example 59c) and 4-fluorobenzonitrile. White solid, ISP-MS: m/e=323.3 ([M+H]+).

b) (S)-4-[4-(3-Hydroxy-pyrrolidin-1-yl)-2,6-dimethyl-quinolin-7-ylmethoxy]-benzonitrile hydrochloride The title compound was produced in accordance with the general method of example 54b from 4-(4-chloro-2,6-dimethyl-quinolin-7-ylmethoxy)-benzonitrile and (S)-3-pyrrolidinol, and isolated as the hydrochloride salt. White solid, ISP-MS: m/e=374.5 ([M−Cl]+).

Example 84

(S)-4-[4-(3-Methoxy-pyrrolidin-1-yl)-2,6-dimethyl-quinolin-7-ylmethoxy]-benzonitrile Sodium hydride (55–65% dispersion in mineral oil, 12 mg, 0.30 mmol) was added to a solution of (S)-4-[4-(3-hydroxy-pyrrolidin-1-yl)-2,6-dimethyl-quinolin-7-ylmethoxy]-benzonitrile hydrochloride (example 83, 58 mg, 0.14 mmol) in N,N-dimethylformamide (1 mL) at 0° C., then after 10 min iodomethane (22 mg, 0.16 mmol) was added. After 90 min the ice bath was removed and the reaction mixture stirred for another 90 min, then partitioned between dichloromethane and 1 M aq. sodium hydroxide solution. The organic layer was washed with brine, dried (MgSO4), and evaporated. Flash chromatography (SiO2, CH2Cl2/MeOH/NH4OH 90:10:0.25) afforded the title compound (27 mg, 49%). White solid, ISP-MS: m/e=388.4 ([M+H]+).

Example 85

(S)-1-[2,6-Dimethyl-7-(tetrahydro-pyran-2-yloxymethyl)-quinolin-4-yl]-pyrrolidin-3-ol hydrochloride a) 4-Chloro-2,6-dimethyl-7-(tetrahydro-pyran-2-yloxymethyl)-quinoline A solution of (4-chloro-2,6-dimethyl-quinolin-7-yl)-methanol (example 59c, 300 mg, 1.35 mmol), 3,4-dihydro-2H-pyran (342 mg, 4.06 mmol), and pyridinium toluene-4-sulfonate (374 mg, 1.49 mg) in dichloromethane (3 mL) and toluene (3 mL) was stirred at r.t. for 3 d, then partitioned between ethyl acetate and water. The organic layer was washed with brine, dried (MgSO4), and evaporated. Flash chromatography (SiO2, hexane/ethyl acetate gradient)

afforded the title compound (243 mg, 59%). White solid, ISP-MS: m/e=306.3 ([M+H]⁺).

b) (S)-1-[2,6-Dimethyl-7-(tetrahydro-pyran-2-yloxymethyl)-quinolin-4-yl]-pyrrolidin-3-ol hydrochloride The title compound was produced in accordance with the general method of example 54b from 4-chloro-2,6-dimethyl-7-(tetrahydro-pyran-2-yloxymethyl)-quinoline and (S)-3-pyrrolidinol, and isolated as the hydrochloride salt. White solid, ISP-MS: m/e=357.4 ([M−Cl]⁺).

Example 86

(S)-4-(3-Methoxy-pyrrolidin-1-yl)-2,6-dimethyl-7-(tetrahydro-pyran-2-yloxymethyl)-quinoline The title compound was produced in accordance with the general method of example 84 from (S)-1-[2,6-dimethyl-7-(tetrahydro-pyran-2-yloxymethyl)-quinolin-4-yl]-pyrrolidin-3-ol hydrochloride (example 85) and iodomethane. Colourless gum, ISP-MS: m/e=371.4 ([M+H]⁺).

Example 87

(6-Methoxy-2-methyl-4-pyrrolidin-1-yl-quinolin-7-yl)-methanol a) 4-Chloro-7-iodo-6-methoxy-2-methyl-quinoline The title compound was produced in accordance with the general method of example 59a from 3-iodo-4-methoxyaniline (*J. Chem. Soc. Perkin* 2 1980, 832) and separated from the isomeric 4-chloro-5-iodo-6-methoxy-2-methyl-quinoline by flash chromatography (SiO₂, hexane/ethyl acetate gradient). White solid, ISP-MS: m/e=334.1 ([M+H]⁺).

b) 4-Chloro-6-methoxy-2-methyl-quinoline-7-carboxylic acid ethyl ester

The title compound was produced in accordance with the general method of example 2b (method B) from 4-chloro-7-iodo-6-methoxy-2-methyl-quinoline. Light brown solid, ISP-MS: m/e=280.2 ([M+H]⁺).

c) (4-Chloro-6-methoxy-2-methyl-quinolin-7-yl)-methanol

The title compound was produced in accordance with the general method of example 2c from 4-chloro-6-methoxy-2-methyl-quinoline-7-carboxylic acid ethyl ester. White solid, EI-MS: m/e=237.2 (M⁺).

d) (6-Methoxy-2-methyl-4-pyrrolidin-1-yl-quinolin-7-yl)-methanol

The title compound was produced in accordance with the general method of example 2d from (4-chloro-6-methoxy-2-methyl-quinolin-7-yl)-methanol and pyrrolidine. White solid, ISP-MS: m/e=273.3 ([M+H]⁺).

Example 88

(6-Methyl-4-pyrrolidin-1-yl-quinolin-7-yl)-methanol a) 7-Iodo-6-methyl-4-oxo-1,4-dihydro-quinoline-3-carboxylic acid ethyl ester A mixture of 3-iodo-4-methylaniline (10.0 g, 42.9 mmol) and diethyl ethoxy methylenemalonate (12.4 g, 57.2 mmol) was heated at 150° C. for 80 min, and the liberated ethanol was allowed to evaporate. After cooling Dowtherm® A (50 mL) was added, then the mixture was heated at 250° C. for 75 min. After cooling to room temperature, heptane (50 mL) was added and the precipitate collected by filtration. The crude material was subsequently triturated in hexane/ethyl acetate (50 mL) and in 70% aqueous ethanol (2×300 mL) to afford the title compound (8.30 g, 54%). White solid, ISP-MS: m/e=358.1 ([M+H]⁺).

b) 7-Iodo-6-methyl-4-oxo-1,4-dihydro-quinoline-3-carboxylic acid

A suspension of 7-iodo-6-methyl-4-oxo-1,4-dihydro-quinoline-3-carboxylic acid ethyl ester (8.30 g, 23.2 mmol) in 2 M aq. sodium hydroxide solution (80 mL) was heated at reflux for 2 h. After cooling the solution obtained was acidified with 25% aq. hydrochloric acid solution. The precipitate was collected by filtration and dried to afford the title compound (7.56 g, 99%). White solid, ISN-MS: m/e=327.9 ([M−H]⁻).

c) 7-Iodo-6-methyl-1H-quinolin-4-one

Under vigorous stirring, 7-iodo-6-methyl-4-oxo-1,4-dihydro-quinoline-3-carboxylic acid (6.50 g, 19.8 mmol) was added portionwise to Dowtherm® A (120 mL) at 250° C., then the mixture was stirred for another 90 min. After cooling, heptane (170 mL) was added, and the precipitate was collected by filtration. The crude material was triturated in hexane/ethyl acetate (1:1) to afford the title compound (5.12 g, 91%). Off-white solid, ISP-MS: m/e=286.1 ([M+H]⁺).

d) 4-Chloro-7-iodo-6-methyl-quinoline

A mixture of 7-iodo-6-methyl-1H-quinolin-4-one (5.12 g, 18.0 mmol), phosphorus oxide chloride (14 mL) and N,N-dimethylformamide (1 mL) was stirred at 60° C. for 80 min, then poured onto ice and carefully neutralized with 25% aq. ammonium hydroxide solution. The suspension was extracted three times with dichloromethane, the combined organic phase was washed with brine, dried (MgSO₄), and evaporated to afford the title compound (5.33 g, 98%). Light brown solid, ISP-MS: m/e=304.1 ([M+H]⁺).

e) 4-Chloro-6-methyl-quinoline-7-carboxylic acid ethyl ester

The title compound was produced in accordance with the general method of example 2b (method B) from 4-chloro-7-iodo-6-methyl-quinoline. Brown solid, ISP-MS: m/e=250.2 ([M+H]⁺).

f) (4-Chloro-6-methyl-quinolin-7-yl)-methanol

The title compound was produced in accordance with the general method of example 2c from 4-chloro-6-methyl-quinoline-7-carboxylic acid ethyl ester. Off-white solid, EI-MS: m/e=189.3 ([M−H₂O]⁺, 100%), 207.2 (M⁺, 34%).

g) (6-Methyl-4-pyrrolidin-1-yl-quinolin-7-yl)-methanol

The title compound was produced in accordance with the general method of example 2d from (4-chloro-6-methyl-quinolin-7-yl)-methanol and pyrrolidine. Light brown solid, ISP-MS: m/e=243.2 ([M+H]⁺).

Example 89

(S)-[4-(3-Methoxy-pyrrolidin-1-yl)-2,6-dimethyl-quinolin-7-yl]-methanol

A solution of (S)-4-(3-methoxy-pyrrolidin-1-yl)-2,6-dimethyl-7-(tetrahydro-pyran-2-yloxymethyl)-quinoline (example 86, 50 mg, 0.14 mmol) and pyridinium toluene-4-sulfonate (37 mg, 0.15 mmol) was stirred at 70° C. for 16 h, then partitioned between ethyl acetate and 1 M aq. sodium hydroxide solution. The organic layer was washed with brine, dried (MgSO₄), and evaporated. Flash chromatography (SiO$_2$, CH$_2$Cl$_2$/MeOH/NH$_4$OH 90:10:0.25) afforded the title compound (26 mg, 67%). White solid, ISP-MS: m/e=287.2 ([M+H]$^+$).

Example 90

4-((S)-3-(Cyclopropylmethoxy)-pyrrolidin-1-yl)-2,6-dimethyl-7-(tetrahydro-pyran-2-yloxymethyl)-quinoline The title compound was produced in accordance with the general method of example 84 from (S)-1-[2,6-dimethyl-7-(tetrahydro-pyran-2-yloxymethyl)-quinolin-4-yl]-pyrrolidin-3-ol hydrochloride (example 85) and (bromomethyl)cyclopropane. Colourless gum, ISP-MS: m/e=371.4 ([M+H]$^+$).

Example 91

4-Azepan-1-yl-2-chloro-6-methyl-7-(3-trifluoromethyl-phenoxymethyl)-quinoline

Diisopropylazodicarboxylate (66 mg, 0.33 mmol) was added dropwise at r.t. to a solution of (4-Azepan-1-yl-2-chloro-6-methyl-quinolin-7-yl)-methanol (example 82, 100 mg, 0.33 mmol), 3-trifluoromethylphenol (53 mg, 0.33 mmol), and triphenylphosphine (86 mg, 0.33 mmol) in dichloromethane (2 mL), then after 2 h ethyl acetate was added and the solution was washed with 1 M aq. sodium hydroxide solution and brine, dried (MgSO$_4$), and evaporated. Flash chromatography (SiO$_2$, hexane/ethyl acetate gradient) yielded the title compound (118 mg, 80%). White solid, ISP-MS: m/e=449.4 ([M+H]$^+$).

Example 92

(S)-4-{[4-(3-Ethoxy-pyrrolidin-1-yl)-2-methyl-quinolin-7-ylmethyl]-amino}-benzonitrile a) 4-[(4-Chloro-2-methyl-quinolin-7-ylmethyl)-amino]-benzonitrile Sodium triacetoxyborohydride (74 mg, 0.34 mmol) was added to a solution of 4-chloro-2-methyl-quinoline-7-carbaldehyde (example 13a, 50 mg, 0.24 mmol), 4-aminobenzonitrile (29 mg, 0.24 mmol), and acetic acid (88 mg, 1.5 mmol) in 1,2-dichloroethane (0.5 mL), then after 16 h the reaction mixture was partitioned between ethyl acetate and 2 M aq. sodium hydroxide solution. The organic layer was washed with brine, dried (MgSO$_4$), and evaporated. Flash chromatography (SiO$_2$, hexane/ethyl acetate 1:1) afforded the title compound (48 mg, 64%). White solid, ISP-MS: m/e=308.2 ([M+H]$^+$).

b) (S)-4-{[4-(3-Ethoxy-pyrrolidin-1-yl)-2-methyl-quinolin-7-ylmethyl]-amino}-benzonitrile The title compound was produced in accordance with the general method of example 54b from 4-[(4-chloro-2-methyl-quinolin-7-ylmethyl)-amino]-benzonitrile and (S)-3-ethoxy-pyrrolidine. White foam, ISP-MS: m/e=387.3 ([M+H]$^+$).

Example 93

(S)-4-[4-(3-Ethoxy-pyrrolidin-1-yl)-2-methyl-quinolin-7-ylmethoxy]-benzonitrile

The title compound was produced in accordance with the general method of example 54b from 4-(4-chloro-2-methyl-quinolin-7-ylmethoxy)-benzonitrile (example 54a) and (S)-3-ethoxypyrrolidine. White foam, ISP-MS: m/e=388.3 ([M+H]$^+$).

Example 94

(S)-[4-(3-(Cyclopropylmethoxy)-pyrrolidin-1-yl)-2,6-dimethyl-quinolin-7-yl]-methanol The title compound was produced in accordance with the general method of example 89 from 4-((S)-3-(cyclopropylmethoxy)-pyrrolidin-1-yl)-2,6-dimethyl-7-(tetrahydro-pyran-2-yloxymethyl)-quinoline (example 90). Light yellow solid, ISP-MS: m/e=327.4 ([M+H]$^+$).

Example 95

N-[4-Azepan-1-yl-6-methyl-7-(3-trifluoromethyl-phenoxymethyl)-quinolin-2-yl]-methyl-amine The title compound was produced in accordance with the general method of example 96 from 4-azepan-1-yl-2-chloro-6-methyl-7-(3-trifluoromethyl-phenoxymethyl)-quinoline (example 91) and methylamine. Light yellow solid, ISP-MS: m/e=444.5 ([M+H]$^+$).

Example 96

[4-Azepan-1-yl-6-methyl-7-(3-trifluoromethyl-phenoxymethyl)-quinolin-2-yl]-dimethyl-amine A mixture of 4-azepan-1-yl-2-chloro-6-methyl-7-(3-trifluoromethyl-phenoxymethyl)-quinoline (example 91, 56 mg, 0.13 mmol) and 33% ethanolic dimethylamine solution (4 mL) was heated at 157° C. for 2 h in a sealed tube using microwave irradiation. After cooling the solution obtained was partitioned between dichloromethane and 2 M aq. sodium hydroxide solution. The organic layer was washed with brine, dried (MgSO$_4$), and evaporated. Flash chromatography (CH$_2$Cl$_2$/MeOH/NH$_4$OH 97.5:2.5:0.2) afforded the title compound (45 mg, 79%). Off-white solid, ISP-MS: m/e=458.5 ([M+H]$^+$).

Example 97

(4-Azepan-1-yl-2-dimethylamino-6-methyl-quinolin-7-yl)-methanol

The title compound was produced in accordance with the general method of example 96 from (4-azepan-1-yl-2-chloro-6-methyl-quinolin-7-yl)-methanol (example 82) and dimethylamine. Light yellow solid, ISP-MS: m/e=314.4 ([M+H]$^+$).

Example 98

(S)-4-[4-(3-(Cyclopropylmethoxy)-pyrrolidin-1-yl)-2,6-dimethyl-quinolin-7-ylmethoxy]-benzonitrile The title compound was produced in accordance with the general method of example 84 from (S)-4-[4-(3-hydroxy-pyrrolidin-1-yl)-2,6-dimethyl-quinolin-7-ylmethoxy]-benzonitrile hydrochloride (example 83) and (bromomethyl)cyclopropane. Light yellow foam, ISP-MS: m/e=428.6 ([M+H]$^+$).

Example 99

4-(6-Methyl-4-pyrrolidin-1-yl-quinolin-7-yl-methoxy)-benzonitrile

The title compound was produced in accordance with the general method of example 6 from (6-methyl-4-pyrrolidin-1-yl-quinolin-7-yl)-methanol (example 88) and 4-fluorobenzonitrile. Off-white solid, ISP-MS: m/e=344.4 ([M+H]$^+$).

Example 100

4-(4-Azepan-1-yl-2-dimethylamino-6-methyl-quinolin-7-ylmethoxy)-benzonitrile

The title compound was produced in accordance with the general method of example 6 from (4-azepan-1-yl-2-dimethylamino-6-methyl-quinolin-7-yl)-methanol (example 97) and 4-fluorobenzonitrile. Off-white solid, ISP-MS: m/e=415.5 ([M+H]$^+$).

Example 101

4-[(2,6-Dimethyl-4-pyrrolidin-1-yl-quinolin-7-ylmethyl)-amino]-benzonitrile a) 4-Chloro-2,6-dimethyl-quinoline-7-carbaldehyde The title compound was produced in accordance with the general method of example 13a (method A) from (4-chloro-2,6-dimethyl-quinolin-7-yl)-methanol (example 59c). White solid, ISP-MS: m/e=220.3 ([M+H]$^+$).

b) 4-[(4-Chloro-2,6-dimethyl-quinolin-7-ylmethyl)-amino]-benzonitrile

The title compound was produced in accordance with the general method of example 92a from 4-chloro-2,6-dimethyl-quinoline-7-carbaldehyde and 4-aminobenzonitrile. White solid, ISP-MS: m/e=322.3 ([M+H]$^+$).

c) 4-[(2,6-Dimethyl-4-pyrrolidin-1-yl-quinolin-7-ylmethyl)-amino]-benzonitrile

The title compound was produced in accordance with the general method of example 56 from 4-[(4-chloro-2,6-dimethyl-quinolin-7-ylmethyl)-amino]-benzonitrile and pyrrolidine. Light yellow foam, ISP-MS: m/e=357.3 ([M+H]$^+$).

Example 102

(S)-4-{[4-(3-Ethoxy-pyrrolidin-1-yl)-2,6-dimethyl-quinolin-7-ylmethyl]-amino}-benzonitrile The title compound was produced in accordance with the general method of example 54b from 4-[(4-chloro-2,6-dimethyl-quinolin-7-ylmethyl)-amino]-benzonitrile (example 101b) and (S)-3-ethoxypyrrolidine. Light yellow foam, ISP-MS: m/e=401.5 ([M+H]$^+$).

Example 103

4-(6-Methyl-4-pyrrolidin-1-yl-quinolin-7-yl-methoxy)-2-trifluoromethyl-benzonitrile The title compound was produced in accordance with the general method of example 6 from (6-methyl-4-pyrrolidin-1-yl-quinolin-7-yl)-methanol (example 88) and 4-fluoro-2-trifluoromethylbenzonitrile. Yellow solid, ISP-MS: m/e=412.3 ([M+H]$^+$).

Example 104

(S)-[4-(3-Ethoxy-pyrrolidin-1-yl)-6-methyl-quinolin-7-yl]-methanol

The title compound was produced in accordance with the general method of example 54b from (4-chloro-6-methyl-quinolin-7-yl)-methanol (example 88f) and (S)-3-ethoxy-pyrrolidine. Yellow solid, ISP-MS: m/e=287.2 ([M+H]$^+$).

Example 105

(S)-4-{[4-(2-Hydroxymethyl-pyrrolidin-1-yl)-2,6-dimethyl-quinolin-7-ylmethyl]-amino}-benzonitrile The title compound was produced in accordance with the general method of example 54b from 4-[(4-chloro-2,6-dimethyl-quinolin-7-ylmethyl)-amino]-benzonitrile (example 101b) and L-prolinol. Light yellow foam, ISP-MS: m/e=387.3 ([M+H]$^+$).

Example 106

4-[(2,6-Dimethyl-4-pyrrolidin-1-yl-quinolin-7-ylmethyl)-methyl-amino]-benzonitrile a) 4-[(4-Chloro-2,6-dimethyl-quinolin-7-ylmethyl)-methyl-amino]-benzonitrile Iodomethane (46 mg, 0.33 mmol) was added to a solution of 4-[(4-chloro-2,6-dimethyl-quinolin-7-ylmethyl)-amino]-benzonitrile (example 101b, 70 mg, 0.22 mmol) in N,N-dimethylformamide (1 mL) at 0° C. The reaction mixture was stirred for 1 h at 0° C. and 1 h at r.t., then partitioned between dichloromethane and 1 M aq. sodium hydroxide solution. The organic layer was washed with brine, dried (MgSO$_4$), and evaporated. Flash chromatography (SiO$_2$, hexane/ethyl acetate 2:1, then 1:1) afforded the title compound (63 mg, 86%). White solid, ISP-MS: m/e=336.2 ([M+H]$^+$).

b) 4-[(2,6-Dimethyl-4-pyrrolidin-1-yl-quinolin-7-ylmethyl)-methyl-amino]-benzonitrile The title compound was produced in accordance with the general method of example 56 from 4-[(4-chloro-2,6-dimethyl-quinolin-7-ylmethyl)-methyl-amino]-benzonitrile and pyrrolidine. White solid, ISP-MS: m/e=371.3 ([M+H]$^+$).

Example 107

(S)-4-[4-(3-Ethoxy-pyrrolidin-1-yl)-6-methyl-quinolin-7-ylmethoxy]-benzonitrile

The title compound was produced in accordance with the general method of example 6 from (S)-[4-(3-ethoxy-pyrrolidin-1-yl)-6-methyl-quinolin-7-yl]-methanol (example 104) and 4-fluorobenzonitrile. Yellow solid, ISP-MS: m/e=388.2 ([M+H]$^+$).

Example 108

(S)-4-[4-(3-Ethoxy-pyrrolidin-1-yl)-6-methyl-quinolin-7-ylmethoxy]-2-trifluoromethyl-benzonitrile; hydrochloride The title compound was produced in accordance with the general method of example 6 from (S)-[4-(3-ethoxy-pyrrolidin-1-yl)-6-methyl-quinolin-7-yl]-methanol (example 104)

and 4-fluoro-2-trifluoromethylbenzonitrile. White solid, ISP-MS: m/e=456.4 ([M−Cl]$^+$).

Example 109 a) (S)-4-(3-Ethoxy-pyrrolidin-1-yl)-6-methyl-quinoline-7-carbaldehyde

The title compound was produced in accordance with the general method of example 79a from (S)-[4-(3-ethoxy-pyrrolidin-1-yl)-6-methyl-quinolin-7-yl]-methanol (example 104). Dark green solid, ISP-MS: m/e=285.1 ([M+H]$^+$).

b) (S)-4-{[4-(3-Ethoxy-pyrrolidin-1-yl)-6-methyl-quinolin-7-ylmethyl]-amino}-2-trifluoromethyl-benzonitrile The title compound was produced in accordance with the general method of example 92a from (S)-4-(3-ethoxy-pyrrolidin-1-yl)-6-methyl-quinoline-7-carbaldehyde and 4-amino-2-trifluoromethylbenzonitrile. Light brown gum, ISP-MS: m/e=455.4 ([M+H]$^+$).

Example 110

(S)-4-{[4-(3-Ethoxy-pyrrolidin-1-yl)-6-methyl-quinolin-7-ylmethyl]-amino}-benzonitrile The title compound was produced in accordance with the general method of example 92a from (S)-4-(3-ethoxy-pyrrolidin-1-yl)-6-methyl-quinoline-7-carbaldehyde (example 109) and 4-aminobenzonitrile. White solid, ISP-MS: m/e=387.2 ([M+H]$^+$).

Example 111

6-Bromo-2-methyl-4-pyrrolidin-1-yl-quinoline-7-carboxylic acid methyl ester a) 4-Bromo-3-methoxy-phenylamine A suspension of iron powder (40.8 g, 0.730 mol), ammonium chloride (64.7 g, 1.21 mol) and 2-bromoanisole (50 g, 0.215 mol) in water (1.5 L) and MeOH (1 L) was stirred overnight at 75° C. The solid was filtered off and the liquid was diluted with ethyl acetate, washed with brine, dried over sodium sulfate, filtered and the solvents were evaporated under vacuum. 43.1 g of the title compound were obtained. Brown solid, ISP-MS: m/e=203.1 ([M+H]$^+$).

b) 5-Amino-2-bromo-phenol

A suspension of 4-bromo-3-methoxy-phenylamine (37.6 g, 0.186 mol) and tetrabutylammonium iodide (96 g, 0.260 mol) in dichloromethane (1.2 L) was cooled down to −78° C. A 1M solution of boron trichloride in dichloromethane (520 mL, 0.521 mol) was added dropwise, within 20 min. The cooling bath was removed. After 3 hours, the reaction mixture was poured onto ice water (4.5 kg). The organic layer was extracted with water. The combined aqueous layers were washed with dichloromethane. The pH was adjusted to 9 using sodium hydrogencarbonate. Sodium chloride was added until saturation. The aqueous layer was extracted with ethyl acetate. The combined organic layers were dried over sodium sulfate, filtered and the solvents were evaporated. The solid was washed with dichloromethane and dried under vacuum. 35.2 g of the title compound were obtained. Brown solid, ISP-MS: m/e=189.1 ([M+H]$^+$).

c) 3-Benzyloxy-4-bromo-phenylamine

To a solution of 5-amino-2-bromo-phenol (35.2 g, 0.187 mol) in N,N-dimethylformamide (350 mL) was added potassium tert-butoxide (22.9 g, 0.204 mol). After 15 min, benzyl chloride (25.5 mL, 0.222 mol) was added within 2 min. The reaction was stirred during 4 h and then poured onto an aqueous solution of sodium hydrogenocarbonate and extracted with ethyl acetate. The combined organic phases were washed with brine and water then dried over sodium sulfate, filtered, and evaporated under vacuum. 55.6 g of the title compound were obtained. Black solid, ISP-MS: m/e=279.1 ([M+H]$^+$).

d) 3-(3-Benzyloxy-4-bromo-phenylamino)-but-2-enoic acid ethyl ester

To a mixture of 3-benzyloxy-4-bromo-phenylamine (55.7 g, 0.168 mol) and ethyl acetoacetate (23.4 mL, 0.185 mol) in cyclohexane was added toluene-4-sulfonic acid monohydrate (0.320 g, 1.68 mmol) The reaction mixture was refluxed during 6 h and the water was azeotropically removed. The reaction mixture was then partitioned between ethyl acetate and an aqueous solution of sodium hydrogenocarbonate. The organic layer was washed with brine, dried over sodium sulfate, filtered and the solvents were evaporated under vacuum. 69.6 g of the title compound were obtained. Black oil, ISP-MS m/e=392.2 ([M+H]$^+$).

e) 7-Benzyloxy-6-bromo-2-methyl-quinolin-4-ol

Dowtherm®A (320 mL) was heated to 250° C. then a solution of 3-(3-benzyloxy-4-bromo-phenylamino)-but-2-enoic acid ethyl ester (55.5 g, 99.5 mmol) in Dowtherm®A (120 mL) was slowly added. The reaction mixture was heated 16 min at 250° C. and ethanol was collected by distillation. The mixture was cooled down, diluted with hexanes (1.5 L) and filtered. The solid was washed with ether and dried under vacuum. 73.0 g of the title compound were obtained. Brown solid, ISP-MS: m/e=345.2 ([M+H]$^+$).

f) 7-Benzyloxy-6-bromo-4-chloro-2-methyl-quinoline

7-Benzyloxy-6-bromo-2-methyl-quinolin-4-ol (25.0 g, 72.6 mmol) and phosphorous oxychloride (70 mL, 0.764 mol) were heated 40 min at 130° C. and then cooled down to room temperature. Phosphorous oxychloride was evaporated under high vacuum. Ice water was added and the pH of this solution was adjusted to 9 with ammonium hydroxide. The suspension was extracted with dichloromethane. The combined organic layers were dried under vacuum. 22.8 g of the title compound were obtained. Brown solid, ISP-MS: m/e=364.0 ([M+H]$^+$).

g) 7-Benzyloxy-6-bromo-2-methyl-4-pyrrolidin-1-yl-quinoline

A mixture of 7-benzyloxy-6-bromo-4-chloro-2-methyl-quinoline (10.0 g, 27.6 mmol) and pyrrolidine (47 mL, 0.562 mol) was refluxed during 3 h. The mixture was cooled down and the pyrrolidine was evaporated under high vacuum. The residue was taken up in dichloromethane, washed with water and brine, dried over sodium sulfate, filtered and the solvents were evaporated under vacuum. 6.9 g of the title compound were obtained. Brown solid, ISP-MS: m/e=399.2 ([M+H]$^+$).

h) 6-Bromo-2-methyl-4-pyrrolidin-1-yl-quinolin-7-ol

To a cooled (0° C.) solution of 7-benzyloxy-6-bromo-2-methyl-4-pyrrolidin-1-yl-quinoline (2.3 g, 5.79 mmol) in dichloromethane (70 mL) was added a 1M solution of titanium tetrachloride in dichloromethane (48.6 mL, 48.6 mmol) within 20 min. After 1 h, the reaction mixture was poured onto an aqueous solution of sodium hydrogenocarbonate, extracted with dichloromethane and evaporated. 1.13 g of the title compound was obtained. Yellow solid, ISP-MS: m/e=308.1 ([M+H]$^+$).

i) Trifluoro-methanesulfonic acid 6-bromo-2-methyl-4-pyrrolidin-1-yl-quinolin-7-yl ester To a cooled (−25° C.) solution of 6-bromo-2-methyl-4-pyrrolidin-1-yl-quinolin-7-ol (350 mg, 1.14 mmol) and triethylamine (0.189 mL, 2.62 mmol) in dichloromethane (1.5 mL) was added trifluoromethylsulfonyl anhydride (0.292 mL, 1.37 mmol) within 20 min. The cooling bath was removed and the reaction mixture was stirred overnight. The mixture was poured onto an aqueous solution of sodium hydrogenocarbonate and extracted with ethyl acetate. The combined organic phases were dried over sodium sulfate, filtered and the solvents were evaporated under vacuum. 341 mg of the title compound were obtained. Brown solid, ISP-MS: m/e=440.2 ([M+H]$^+$).

j) 6-Bromo-2-methyl-4-pyrrolidin-1-yl-quinoline-7-carboxylic acid methyl ester

A suspension of trifluoro-methanesulfonic acid 6-bromo-2-methyl-4-pyrrolidin-1-yl-quinolin-7-yl ester (160 mg, 0.364 mmol), triethylamine (0.030 μL, 0.4 mmol), palladium acetate (8 mg, 0.036 mmol) and bis-(1,3-diphenylphosphino)propane (16 mg, 0.039 mmol) in dimethylsulfoxide (0.5 mL) and methanol (0.4 mL), under a carbon monoxide atmosphere, was heated to 65° C. for 90 min. The reaction was poured unto an aqueous solution of sodium hydrogenocarbonate and extracted with ethyl acetate. The combined organic layers were dried over sodium sulfate, filtered and the solvents were removed under vacuum. 124 mg of the title compound were obtained. Brown solid, ISP-MS: m/e=429.2 ([M+H]$^+$).

Example 112

(6-Bromo-2-methyl-4-pyrrolidin-1-yl-quinolin-7-yl)-methanol

The title compound was produced in accordance with the general method of example 2c from 6-bromo-2-methyl-4-pyrrolidin-1-yl-quinoline-7-carboxylic acid methyl ester (example 111). Light yellow solid, ISP-MS: m/e=321.2 ([M+H]$^+$).

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example C

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example D

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example E

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:

1. A compound of formula I or a pharmaceutically acceptable salt or ester thereof wherein formula I is:

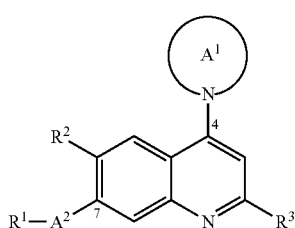

(I)

wherein:
R¹ is —O—R⁴ or —NR⁵R⁶;
R² is hydrogen, alkyl, cycloalkyl, alkoxy, halogen, heterocyclyl or amino;
R³ is hydrogen, alkyl, amino or halogen;
R⁴ is hydrogen, alkyl, cycloalkyl, aryl, aralkyl, cycloalkylalkyl, alkoxyalkyl, hydroxyalkyl or heterocyclyl;
R⁵ and R⁶ are independently selected from the group consisting of hydrogen, alkyl, cycloalkyl, aryl, aralkyl, cycloalkylalkyl, alkoxyalkyl, hydroxyalkyl and heterocyclyl;
or R⁵ and R⁶ together with the N atom to which they are attached form a 5- to 10-membered heterocyclic ring optionally containing a second heteroatom selected from the group consisting of nitrogen, oxygen and sulfur, wherein the heterocyclyc ring is optionally substituted with one or more substituents independently selected from the group consisting of alkyl and alkoxy;
A¹ is a diazepine ring optionally substituted by one to three substituents independently selected from the group consisting of alkyl, alkoxy, hydroxy, hydroxyalkyl, alkoxyalkyl, amino, acetylamino, cyano, tetrahydropyranyloxyalkyl and cycloalkylalkoxy and cycloalyklalkoxy; and
A² is —CH₂— or —C(O)—.

2. The compound according to claim 1, wherein:
A¹ is optionally substituted by one to three substituents independently selected from the group consisting of alkyl, alkoxy, hydroxy, hydroxyalkyl, alkoxyalkyl, amino, acetylamino and cyano.

3. The compound according to claim 1, wherein R² is hydrogen or methyl.

4. The compound according to claim 1, wherein R¹ is —O—R⁴.

5. The compound according to claim 1, wherein R¹ is —NR⁵R⁶.

6. The compound according to claim 1, wherein R³ is alkyl.

7. The compound according to claim 6, wherein R³ is methyl.

8. The compound according to claim 1, wherein R⁴ is hydrogen, alkyl, alkoxyalkyl, pyridinyl, pyrrolidinyl, tetrahydropyranyl, or phenyl optionally substituted with one to three substituents independently selected from the group consisting of alkyl, cyano, trifluoromethyl, alkoxy, halogen, pyrrolidinylcarbonyl and nitro.

9. The compound according to claim 1, wherein one of R⁵ and R⁶ is hydrogen, aryl or alkoxyalkyl and the other is hydrogen or alkyl; or R⁵ and R⁶ together with the N atom to which they are attached form a pyrrolidine ring.

10. The compound according to claim 1, wherein A¹ is optionally substituted by alkyl or amino.

11. The compound according to claim 1, wherein A² is —CH₂—.

12. A process for the preparation of a compound according to claim 1, comprising:

reacting a compound of formula Q1 in the presence of an amine of the formula Q2 in order to obtain a compound according to formula Q3 wherein R¹, R², A¹ and A² are defined as in claim 1 and R³⁰ is hydrogen, alkyl or halogen and Y is chloro, bromo or iodo.

13. A process for the preparation of a compound according to claim 1, comprising:

reacting a compound of formula H in the presence of hydrogen peroxide in order to obtain a compound according to formula ID -continued

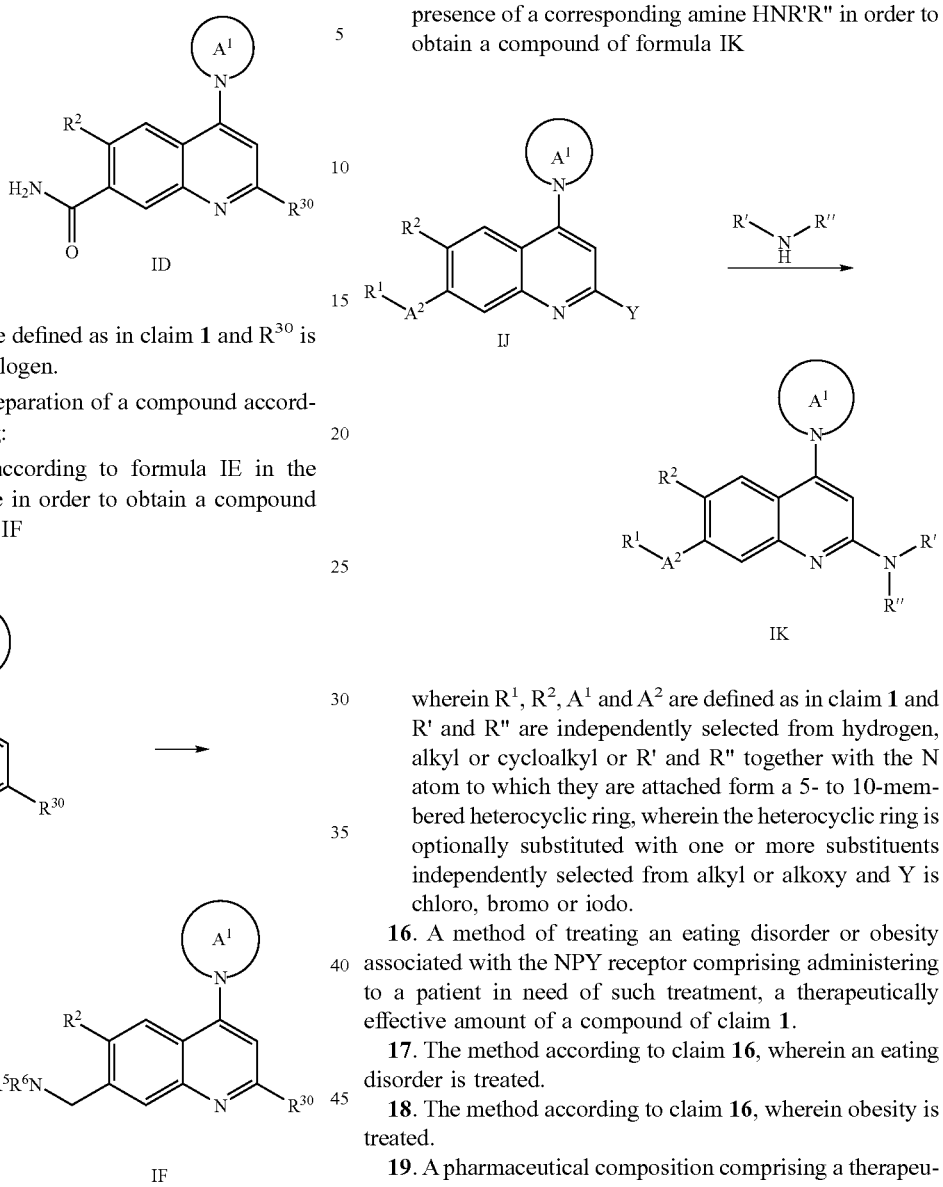

wherein $R^2$ and $A^1$ are defined as in claim 1 and $R^{30}$ is hydrogen, alkyl or halogen.

14. A process for the preparation of a compound according to claim 1, comprising:

reacting a compound according to formula IE in the presence of a hydride in order to obtain a compound according to formula IF wherein $R^2$, $R^5$, $R^6$ and $A^1$ are defined as in claim 1 and wherein $R^{30}$ is hydrogen, alkyl or halogen.

15. A process for the preparation of a compound according to claim 1, comprising:

reacting a compound according to formula IJ in the presence of a corresponding amine HNR'R" in order to obtain a compound of formula IK wherein $R^1$, $R^2$, $A^1$ and $A^2$ are defined as in claim 1 and R' and R" are independently selected from hydrogen, alkyl or cycloalkyl or R' and R" together with the N atom to which they are attached form a 5- to 10-membered heterocyclic ring, wherein the heterocyclic ring is optionally substituted with one or more substituents independently selected from alkyl or alkoxy and Y is chloro, bromo or iodo.

16. A method of treating an eating disorder or obesity associated with the NPY receptor comprising administering to a patient in need of such treatment, a therapeutically effective amount of a compound of claim 1.

17. The method according to claim 16, wherein an eating disorder is treated.

18. The method according to claim 16, wherein obesity is treated.

19. A pharmaceutical composition comprising a therapeutically effective amount of a compound of claim 1 and a pharmaceutically acceptable carrier.

* * * * *